US009260430B2

(12) United States Patent
Moran

(10) Patent No.: US 9,260,430 B2
(45) Date of Patent: Feb. 16, 2016

(54) USE OF TRPA1 ANTAGONISTS TO PREVENT OR TREAT INFECTIONS CAUSED BY BIOLOGICAL-WARFARE AGENTS

(75) Inventor: Magdalene M. Moran, Brookline, MA (US)

(73) Assignee: HYDRA BIOSCIENCES, INC., Cambridge, MA (US)

( * ) Notice: Subject to any disclaimer, the term of this patent is extended or adjusted under 35 U.S.C. 154(b) by 0 days.

(21) Appl. No.: 13/702,488

(22) PCT Filed: Jun. 8, 2011

(86) PCT No.: PCT/US2011/039604
§ 371 (c)(1),
(2), (4) Date: Aug. 1, 2013

(87) PCT Pub. No.: WO2012/050641
PCT Pub. Date: Apr. 19, 2012

(65) Prior Publication Data
US 2013/0310345 A1 Nov. 21, 2013

Related U.S. Application Data

(60) Provisional application No. 61/352,627, filed on Jun. 8, 2010.

(51) Int. Cl.
*A61K 31/522* (2006.01)
*A61K 31/52* (2006.01)
*C07D 473/08* (2006.01)
*A61K 31/65* (2006.01)

(52) U.S. Cl.
CPC ............ *C07D 473/08* (2013.01); *A61K 31/522* (2013.01); *A61K 31/65* (2013.01)

(58) Field of Classification Search
CPC ..... A61K 31/522; A61K 31/65; C07D 473/08
USPC ...................... 514/154, 263.2, 263.23, 263.35
See application file for complete search history.

(56) References Cited

U.S. PATENT DOCUMENTS

| 7,671,061 | B2 * | 3/2010 | Moran et al. ............. 514/263.35 |
| 8,362,025 | B2 * | 1/2013 | Ng et al. .................... 514/263.2 |
| 2009/0023773 | A1 | 1/2009 | Vohra et al. |
| 2011/0144137 | A1 * | 6/2011 | Jordt et al. ............... 514/263.35 |
| 2012/0108614 | A1 * | 5/2012 | Chong ...................... 514/263.23 |
| 2013/0165427 | A1 * | 6/2013 | Chong ...................... 514/217.06 |
| 2013/0303521 | A1 * | 11/2013 | Chong ...................... 514/217.06 |

FOREIGN PATENT DOCUMENTS

WO     2009137087 A2     11/2009

OTHER PUBLICATIONS

Kerstein et al., Pharmacological blockade of TRPA1 inhibits mechanical firing in nociceptors, Apr. 2009, Molecular Pain, vol. 5, No. 9, pp. 1-13.*
Bessac et al. "Breathtaking TRP Channels: TRPA1 and TRPV1 in Airway Chemosensation and Reflex Control" Physiology (2008) vol. 23, No. 6, pp. 360-370.
International Search Report for International Application No. WO2012/050641 dated Apr. 3, 2012.

* cited by examiner

*Primary Examiner* — My-Chau T Tran
(74) *Attorney, Agent, or Firm* — Lando & Anastasi LLP

(57) ABSTRACT

Provided are methods for preventing and treating injuries caused by exposure to biological warfare agents. The methods include administering to a subject in need thereof an effective amount of a TRPA1 antagonist or a pharmaceutically acceptable salt thereof. In an embodiment the TRPA1 antagonist is selected from the group consisting of compounds of formula I $$X-(\overset{R}{\underset{R}{C}})_m-L-(\overset{R}{\underset{R}{C}})_n-R^3 \quad \text{I}$$

and compounds of formula II $$\text{II}$$

Figure 1:
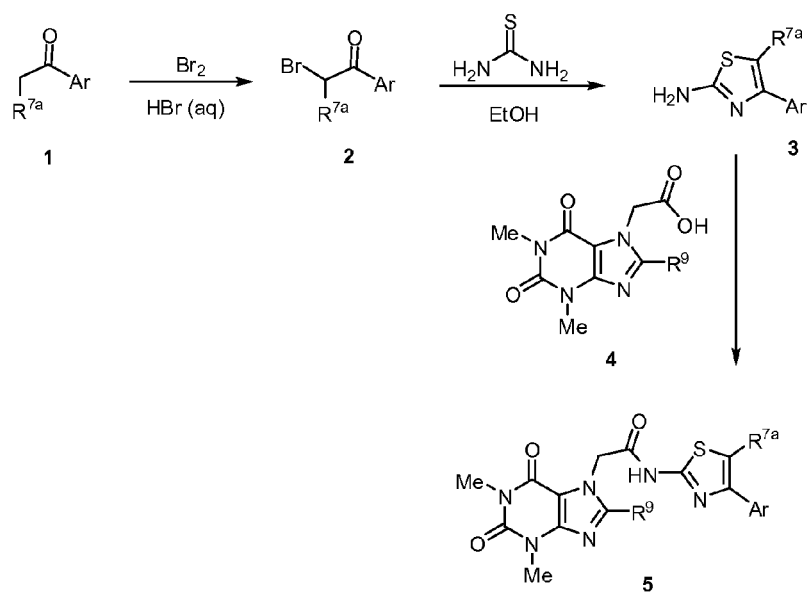

as described herein.

14 Claims, 3 Drawing Sheets

USE OF TRPA1 ANTAGONISTS TO PREVENT OR TREAT INFECTIONS CAUSED BY BIOLOGICAL-WARFARE AGENTS

RELATED APPLICATIONS

This application is the U.S. national phase of International Patent Application No. PCT/US2011/039604, filed Jun. 8, 2011, which claims the benefit of priority of U.S. application Ser. No. 61/352,627, filed Jun. 8, 2010.

BACKGROUND

A variety of ion channel proteins exist to mediate ion flux across cellular membranes. The proper expression and function of ion channel proteins is essential for the maintenance of cell function and intracellular communication. Numerous diseases and disorders are the result of misregulation of membrane potential or aberrant calcium handling. Given the central importance of ion channels in modulating membrane potential and ion flux in cells, identification of agents that can promote or inhibit particular ion channels is of great interest because such compounds can function both as research tools and as therapeutic agents.

SUMMARY

The present invention relates to compounds, compositions and methods for preventing or treating injuries caused by biological warfare and similar agents. One aspect of the invention provides compounds and compositions for preventing or treating injuries resulting from biological-warfare agents by modulating the activity of the TRPA1 channel. In another aspect, the invention features a method of preventing or treating an injury resulting from exposure to a biological-warfare agent, comprising administering to a subject in need thereof an effective amount of a compound, wherein the compound is a TRPA1 antagonist. In some embodiments, the biological-warfare agent is a bacterium that causes anthrax or a bacterium that causes plague. In some embodiments, the compound is administered orally, via intramuscular injection, by topical ocular administration, topically, or by inhalation. In some embodiments, the subject being treated is a human. Additional aspects, embodiments, and advantages of the invention are discussed below in detail.

BRIEF DESCRIPTION OF THE FIGURES

FIG. 1 depicts a general synthetic scheme for the preparation of members of a structural class of TRPA1 antagonists.

FIG. 2 depicts structures of selected TRPA1 antagonists, including HC-030031 (40).

FIG. 3 is a graph depicting survival in a mouse model of plague in which animals received no treatment, low-dose doxycycline alone, HC-030031 (40) followed by low-dose doxycycline, or high-dose ciprofloxacin (Cipro) alone. X-axis, time in days.

DETAILED DESCRIPTION

The present invention provides a strategy to protect mammals (e.g., members of the military and the public) from injury from biological-warfare weapons, particularly infective agents such as the bacteria that cause plague and anthrax. Remarkably, we have discovered that TRPA1 antagonists provide a defense against biological-warfare weapons as they provide general immune enhancement, thus providing an increased defense against a wide variety of biological threats. Furthermore, many TRPA1 antagonists are readily stored as they are both pharmaceutically stable and relatively compact, making it easy to hold them in reserve for use in case of a threatened or suspected biological-warfare attack. In addition, some TRPA1 antagonists can be used without significant side effects, making them more readily usable in situations where it is uncertain whether or not a biological attack or natural infectious outbreak has occurred. Finally, in addition to their effectiveness when used alone, TRPA1 antagonists can enhance the effectiveness of other medical countermeasures such as vaccines and antibiotics. For example, TRPA1 antagonist administration in combination with a tetracycline antibiotic increased the survival rate for animals infected with plague, suggesting that immunomodulator intervention can also provide time for other antimicrobial therapies to be initiated.

TRPA1 antagonists may be used either as prophylactics before exposure and/or as part of a treatment regimen following exposure to biological-warfare agents, providing two complementary strategies to protect the public from a pathogenic challenge. Use of TRPA1 antagonists may also enhance the effectiveness of other medical countermeasures, such as vaccines, immune sera, and/or antibiotics.

Administration of a TRPA1 antagonist with an antibiotic significantly increased the survival of animals exposed to the pathogen that causes plague. For example, survival rate for animals exposed to lethal airborne dosages of plague are only 20% using traditional antibiotic therapies. However, the present invention provides a potential survival rate of about 80% using TRPA1 inhibitors in conjunction with antibiotics.

Accordingly, the present invention provides a method of preventing injury from biological-warfare agents in humans or animals by administering a prophylactically or therapeutically an effective amount of a TRPA1 antagonist. In certain embodiments, the invention provides a method of treating or preventing pathogenesis of infection in humans or animals by one or more infectious agents by administering prophylactically or therapeutically an effective amount of a TRPA1 antagonist. The TRPA1 antagonist may be administered orally, topically, subcutaneously, intramuscularly, transdermally, intradermally, intravenously, or through the gastrointestinal tract.

TRPA1 antagonists may be administered, either before or after exposure to pathogen, in amounts from about 0.1 mg/kg to about 100 mg/kg, or about 0.1 mg/kg to about 500 mg/kg, or a combination thereof. In certain embodiments, the TRPA1 antagonists is administered in amounts from about 1 mg/kg to about 10 mg/kg, or about 2 mg/kg to about 20 mg/kg, or a combination thereof.

The present invention provides potent prevention or treatment of infection by the type of infectious agents expected to be used by bioterrorists. These infectious agents include agents such as those listed as category A, B, and C biological-warfare agents by the US CDC. Such infectious agents include, but are not limited to, *B. anthracis* (anthrax), Brucellosis, *Burkholderia mallei* (glanders), Cholera, *Clostridium perfringens* Toxins, Congo-Crimean Hemorrhagic Fever, Ebola Hemorrhagic Fever, Melioidosis, Plague *Yersinia pestis*, Q Fever, Ricin, Rift Valley Fever, Saxitoxin, Smallpox, Staphylococcal Enterotoxin B, Trichothecene Mycotoxins, Tularemia, Venezuelan Equine Encephalitis Virus, Viral Hemorrhagic fever, Nipah virus, Hantaviruses, yellow fever, multidrug-resistant tuberculosis, Marburg Virus and Dengue Virus. In certain embodiments, the present invention provides a method of treating and preventing infection of humans and animals by *B. anthracis*. Additionally, TRPA1 antagonists have the potential to prevent or treat infections caused by infectious agents that may not be attributed to bioterrorists, including infectious agents that may be drug resistant and/or drug sensitive.

The present invention also provides a method of preventing injury from biological-warfare agents in humans or animals by administering prophylactically or therapeutically an effective amount of a TRPA1 antagonist. Amounts of TRPA1 antagonists may be the same as those listed above for use in preventing infection. In alternate embodiments, the present invention also provides methods of preventing injury from biological-warfare agents in humans or animals by administering prophylactically or therapeutically an effective amount of a synergistic combination of a TRPA1 antagonist and an antibiotic, or by delivering an effective amount of a TRPA1 antagonist subsequent to vaccination against biological-warfare agents or treatment with immune sera or monoclonal antibodies against said biological-warfare agents.

Finally, the present invention provides a composition comprising a TRPA1 antagonist. The availability of stable anti-infective agents helps make TRPA1 antagonists ideal for stockpiling for use against a potential bioterrorist attack.

1. DEFINITIONS

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The definition of each expression, e.g., alkyl, m, n, and the like, when it occurs more than once in any structure, is intended to be independent of its definition elsewhere in the same structure.

The terms "antagonist" and "inhibitor" are used interchangeably to refer to an agent that decreases or suppresses a biological activity, such as to repress an activity of an ion channel, such as TRPA1. TRPA1 inhibitors include inhibitors having any combination of the structural and/or functional properties disclosed herein.

An "effective amount" of, e.g., a TRPA1 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPA1 antagonist for use in the methods of the present invention, includes an amount of a TRPA1 antagonist effective to decrease one or more in vitro or in vivo function of a TRPA1 channel. Exemplary functions include, but are not limited to, membrane polarization (e.g., an antagonist may promote hyperpolarization of a cell), ion flux, ion concentration in a cell, outward current, and inward current. Compounds that antagonize TRPA1 function include compounds that antagonize an in vitro or in vivo functional activity of TRPA1. When a particular functional activity is only readily observable in an in vitro assay, the ability of a compound to inhibit TRPA1 function in that in vitro assay serves as a reasonable proxy for the activity of that compound. In certain embodiments, an effective amount is an amount sufficient to inhibit a TRPA1-mediated current and/or the amount sufficient to inhibit TRPA1 mediated ion flux.

The TRPA1 inhibitors for use in the methods of the present invention may be characterized according to their activity, or lack of activity, against one or more other ion channels. When other ion channels are referred to, inhibition of a function of such other ion channels is defined similarly. For example, inhibition of an ion channel or an activity of an ion channel means the antagonist inhibits one or more functional activities of the other ion channel. Such functions include the current mediated by the particular ion channel, ion flux, or membrane polarization.

The terms "compound" and "agent" are used interchangeably to refer to the inhibitors/antagonists of the invention. In certain embodiments, the compounds are small organic or inorganic molecules, e.g., with molecular weights less than 7500 amu, preferably less than 5000 amu, and even more preferably less than 2000, 1500, 1000, or 500 amu. One class of small organic or inorganic molecules are non-peptidyl, e.g., containing 2, 1, or no peptide and/or saccharide linkages. In certain other embodiments, the compounds are peptidyl agents such as polypeptides or antibodies. In certain other embodiments, the compounds are proteins, for example, antibodies or aptamers. Such compounds can bind to and inhibit a function of TRPA1. In certain other embodiments, the compounds are nucleic acids, for example, TRPA1 antisense oligonucleotides or TRPA1 RNAi constructs. Such compounds can inhibit the expression of TRPA1, thereby inhibiting the activity of TRPA1. Other exemplary compounds that may act as inhibitors include ribozymes and peptide fragments.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The term "oxidative metabolite" is intended to encompass compounds that are produced by metabolism of the parent compound under normal physiological conditions. Specifically, an oxidative metabolite is formed by oxidation of the parent compound during metabolism. For example, a thioether group may be oxidized to the corresponding sulfoxide or sulfone.

The term "solvate" as used herein, refers to a compound formed by solvation (e.g., a compound formed by the combination of solvent molecules with molecules or ions of the solute).

The term "hydrate" as used herein, refers to a compound formed by the union of water with the parent compound.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal), then the treatment is prophylactic (i.e., it protects the host against developing the unwanted condition). Whereas, if it is administered after manifestation of the unwanted condition, then the treatment is therapeutic (i.e., it is intended to diminish, ameliorate, or stabilize the existing unwanted condition or side effects thereof).

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "lower" when associated with any of the groups listed below indicates that the group contains less than seven carbons (i.e., six carbons or less). For example "lower alkyl" refers to an alkyl group containing 1-6 carbons, and "lower alkenyl" refers to an alkenyl group containing 2-6 carbons.

Exemplary monocyclic rings include furan, thiophene, pyrrole, pyrroline, pyrrolodine, oxazole, thiazole, imidazole, imidazoline, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, and trithiane.

Exemplary bicyclic rings include indolizinyl, indolyl, isoindolyl, indolinyl, benzofuranyl, benzothiophenyl, indazolyl, benzimidazolyl, benthiazolyl, purinyl, quinolizinyl, quinolinyl, isoquinolinyl, cinnolinyl, phthalazinyl, quinazolinyl, quinoxalinyl, naphthyridinyl, pteridinyl, indenyl, naphthalenyl, azulenyl, imidazopyridazionyl, pyrazolopyrimidinedionyl, or pyrrolopyrimidinedionyl moieties.

Exemplary tricyclic rings include carbazole, acridine, phenazine, phenothiazine, phenoxazine, fluorene, and anthracene.

The term "aromatic" refers to a cyclic or polycyclic structure characterized by a cyclically conjugated molecular moiety containing 4n+2 electrons, wherein n is a positive integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon. The term "hydrocarbyl" refers to a hydrocarbon radical.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl.

The term "alkylene" is art-recognized, and as used herein pertains to a bidentate moiety obtained by removing two hydrogen atoms of an alkyl group, as defined above.

The term "alkenyl" as used herein means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "carbocyclyl" as used herein means monocyclic or multicyclic (e.g., bicyclic, tricyclic, etc.) hydrocarbons containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, haloalkyenyl, fluoroalkyl, hydroxy, alkoxy, alkyenyloxy, alkynyloxy, carbocycyloxy, heterocycyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g., methylene).

The term "aryl," as used herein means an aromatic radical (e.g., a phenyl, naphthyl or anthracenyl group). The aryl groups of the present invention can be optionally substituted with 1, 2, 3, 4 or 5 substituents independently selected from the group consisting of alkyl, alkenyl, alkynyl, halo, haloalkyl, haloalkenyl, fluoroalkyl, hydroxy, alkoxy, alkyenyloxy, alkynyloxy, carbocycyloxy, heterocycyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the aryl group through an alkylene moiety (e.g., methylene).

The term "arylene," is art-recognized, and as used herein pertains to a bidentate moiety obtained by removing two hydrogen atoms of an aromatic ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-yl-ethyl.

The term "heteroaryl" as used herein includes aromatic radicals, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b) thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo [2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, haloalkenyl, fluoroalkyl, hydroxy, alkoxy, alkyenyloxy, alkynyloxy, carbocycyloxy, heterocycyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g., methylene).

The term "heteroarylene," is art-recognized, and as used herein pertains to a bidentate moiety obtained by removing two hydrogen atoms of a heteroaromatic ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl) ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein at least one hydrogen is replaced with fluorine.

The term "haloalkenyl" means an alkenyl group, as defined herein, wherein at least one hydrogen is replaced with a halogen, as defined herein. Representative examples of haloalkenyl include, but are not limited to, —C(CF$_3$)=CH (CH$_3$), and —CH$_2$C(CF$_3$)=CH(CF$_3$).

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkyenyloxy", "alkynyloxy", "carbocycyloxy", and "heterocycyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethyl-phenylethoxy, and 2,3-dimethylpyridinylmethoxy.

The term "sulfhydryl" or "thioyl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkyenylthio", "alkynylthio", "carbocyclthio", and "heterocycylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through an sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluoroalkylsulfonyl", "alkenylsulfonyl", "alkynylsulfonyl", "carbocycylsulfonyl", "heterocycylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocycyloxysulfonyl", "heterocycyloxysulfonyl", "aryloxysulfonyl", "aralkyloxysulfonyl", "heteroaryloxysulfonyl" and "heteroaralkyloxysulfonyl" are likewise defined.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O)H group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocycylcarbonyl", "heterocycylcarbonyl", "arylcarbonyl", "aralkylcarbonyl", "heteroarylcarbonyl", and "heteroaralkylcarbonyl" are likewise defined.

The term "acyl" is art-recognized and refers to a group represented by the general formula hydrocarbylC(O)—, preferably alkylC(O)—.

The term "carboxy" as used herein means a —CO$_2$H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocycyloxycarbonyl", "heterocycyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocycylcarbonyloxy", "heterocycylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "carbocycylsulfonyloxy", "heterocycylsulfonyloxy", "arylsulfonyloxy", "aralkylsulfonyloxy", "heteroarylsulfonyloxy", "heteroaralkylsulfonyloxy", "haloalkoxysulfonyloxy", "fluoroalkoxysulfonyloxy", "alkenyloxysulfonyloxy", "alkynyloxysulfonyloxy", "carbocycyloxysulfonyloxy", "heterocycyloxysulfonyloxy", "aryloxysulfonyloxy", "aralkyloxysulfonyloxy", "heteroaryloxysulfonyloxy" and "heteroaralkyloxysulfonyloxy"

The term "amino" as used herein refers to —NH$_2$ and substituted derivatives thereof wherein one or both of the hydrogens are independently replaced with substituents selected from the group consisting of alkyl, haloalkyl, haloalkenyl, fluoroalkyl, alkenyl, alkynyl, carbocycyl, heterocycyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocycylcarbonyl, heterocycylcarbonyl, arylcarbonyl, aralkylcarbonyl, heteroarylcarnbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a —C≡N group.

The term "nitro" as used herein means a —NO$_2$ group.

The term "azido" as used herein means a —N$_3$ group.

The term "phosphoryl" as used herein refers to —P(=O)OH$_2$ and substituted derivatives thereof wherein one or both of the hydroxyls are independently replaced with substituents selected from the group consisting of alkyl, haloalkyl, haloalkenyl, fluoroalkyl, alkenyl, alkynyl, carbocycyl, heterocycyl, aryl, aralkyl, heteroaryl, heteroaralkyl, alkoxy, haloalkoxy, fluoroalkyloxy, alkenyloxy, alkynyloxy, carbocycyloxy, heterocycyloxy, aryloxy, aralkyloxy, heteroaryloxy, heteroaralkyloxy, and amino.

The term "silyl" as used herein includes H$_3$Si— and substituted derivatives thereof wherein one, two or three of the hydrogens are independently replaced with substitutents selected from alkyl, haloalkyl, haloalkenyl, fluoroalkyl, alkenyl, alkynyl, carbocycyl, heterocycyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Contemplated equivalents of the compounds described above include compounds which otherwise correspond thereto, and which have the same general properties thereof (e.g., the ability to inhibit TRPA1 activity), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, trifluoroacetic, propionic, isobutyric, maleic, malonic, benzoic, succinic, suberic, fumaric, lactic, mandelic, phthalic, benzensulfonic, p-tolylsulfonic, citric, tartaric, methanesulfonic, and the like. Also included are the salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "low enough pyrogen activity", with reference to a pharmaceutical preparation, refers to a preparation that does not contain a pyrogen in an amount that would lead to an adverse effect (e.g., irritation, fever, inflammation, diarrhea, respiratory distress, endotoxic shock, etc.) in a subject to which the preparation has been administered. For example, the term is meant to encompass preparations that are free of, or substantially free of, an endotoxin such as, for example, a lipopolysaccharide (LPS).

2. METHODS OF PREVENTION OR TREATMENT USING TRPA1 ANTAGONISTS

One aspect of the invention relates to a method of preventing or treating an injury resulting from exposure to a biological-warfare agent, comprising administering to a subject in need thereof an effective amount of a TRPA1 antagonist or a pharmaceutically acceptable salt thereof.

An antagonist of TRPA1 function may inhibit the outward current, the inward current, or both currents. Compounds that inhibit both currents may do so with the same or with differing $IC_{50}$ values. The extent of inhibition of a particular current is measured by the ability to inhibit or reduce such current (e.g., inward and/or outward) in an in vitro or an in vivo assay. Compounds that inhibit any of the foregoing currents in an in vitro or in vivo assay are characterized as compounds that inhibit a function of TRPA1. Additionally or alternatively, a further exemplary function of TRPA1 that may be inhibited by the present compounds is ion flux mediated by TRPA1.

The antagonist may be chosen because it inhibits a TRPA1 function with an $IC_{50}$ less than or equal to 10 micromolar (μM), 5 μM, 1 μM, or less than or equal to 700, 600, 500, 400, 300, 250, 200, or 100 nM. In other embodiments, the antagonist inhibits a TRPA1 function with an $IC_{50}$ less than or equal to 75 nM, less than or equal to 50 nM, or less than or equal to 25, 10, 5, or 1 nM.

In certain embodiments, inhibition of TRPA1 function means that a function, for example a TRPA1-mediated current, is decreased by greater than 50% in the presence of an effective amount of a compound in comparison to in the absence of the compound or in comparison to an ineffective amount of a compound. In certain other embodiments, the inhibition of a TRPA1 function means that a function, for example a TRPA1-mediated current or TRPA1 mediated ion flux, is decreased by at least 50%, 60%, 70%, 75%, 80%, 85%, or 90% in the presence of an effective amount of a compound in comparison to in the absence of the compound. In still other embodiments, the inhibition of a TRPA1 function means that a function, for example a TRPA1-mediated current, is decreased by at least 92%, 95%, 97%, 98%, 99%, or 100% in the presence of an effective amount of a compound in comparison to in the absence of the compound.

The antagonist can be characterized by some level of activity versus other ion channels (e.g., certain compounds are selective for inhibiting TRPA1 and other compounds exhibit a level of cross reactivity against one or more other ion channel). When a small molecule is characterized by its activity against another ion channel, inhibition of a function or activity of the other ion channel is defined analogously to the way in which a function of a TRPA1 channel is defined. Thus, inhibiting the function of another ion channel means, for example, inhibiting ion flux mediated by that other ion channel or inhibiting the current mediated by that other ion channel.

In some embodiments, a TRPA1 antagonist is chosen for use because it is more selective for one TRP isoform than others, e.g., 10-fold, and more preferably at least 20-, 40-, 50-, 60-, 70-, 80-, or at least 100- or 1000-fold more selective for TRPA1 over one or more of TRPC6, TRPV5, TRPV6, TRPM8, TRPV1, TRPV2, TRPV4, and/or TRPV3. In other embodiments, the differential is smaller, e.g., it more strongly inhibits TRPA1 than TRPM8, TRPV1, TRPV2, TRPV3, and/or TRPV4, preferably at least twice, three times, five times, or ten times more strongly. Such comparisons may be made, for example, by comparing $IC_{50}$ values.

In other embodiments, a small molecule TRPA1 antagonist is chosen for use because it is more selective for TRPA1 than for other non-TRP ion channels, e.g., 10-fold, and more preferably at least 20, 40, 50, 60, 70, 80, or at least 100- or 1000-fold more selective for TRPA1 over one or more of NaV1.2, Cav1.2, Cav3.1, HERG, and/or mitochondrial uniporter. In other embodiments, the differential is smaller, e.g., it more strongly inhibits TRPA1 than NaV1.2, Cav1.2, Cav3.1, HERG, and/or mitochondrial uniporter, preferably at least twice, three times, five times, or ten times more strongly.

In certain embodiments, the subject TRPA1 antagonists inhibit TRPA1 with an $IC_{50}$ at least one order of magnitude more potent than its Ki for the alpha-amino-3-hydroxy-5-methyl-4-isoxazolepropionic acid (AMPA) receptor. In certain other embodiments, the subject TRPA1 antagonists inhibit TRPA1 with an $IC_{50}$ at least two orders of magnitude, three orders of magnitude, or four orders of magnitude more potent than its Ki for the AMPA receptor. In certain embodiments, the subject TRPA1 antagonists do not appreciably bind the AMPA receptor. In other words, the subject antagonists inhibit TRPA1 with a particular $IC_{50}$ and, when administered at that concentration, the antagonist does not appreciably bind the AMPA receptor.

In certain embodiments, a small molecule is chosen because it antagonizes the function of TRPA1 and the function of TRPM8, TRPV1 and/or TRPV3. Although such compounds selectively antagonize the function of more than one ion channel, the $IC_{50}$ values for the different ion channels need not be identical.

The $IC_{50}$ values are measured in vitro using, for example, patch clamp analysis or standard measurements of calcium flux. Exemplary in vitro methods for calcium flux-based $IC_{50}$ estimation are described in Example 2. Methods used to obtain more definitive $IC_{50}$ measurements are described in Example 3. Alternatively, estimates of % inhibition of current or ion flux can also be calculated and used to assess efficacy of a compound as an inhibitor.

Figure 2:
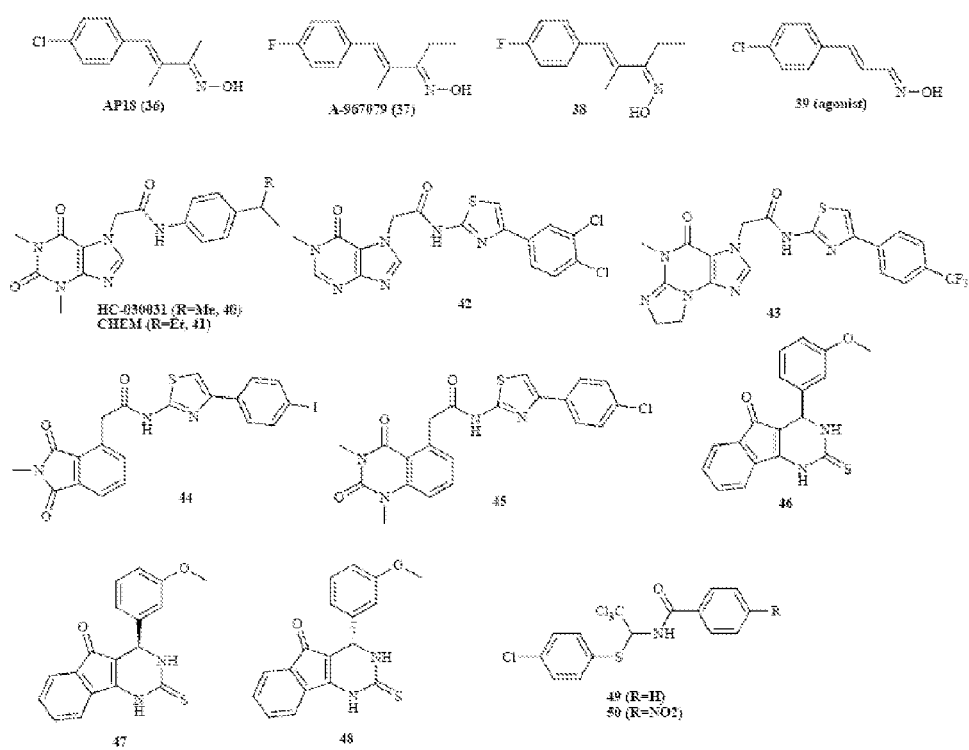
Figure 3:
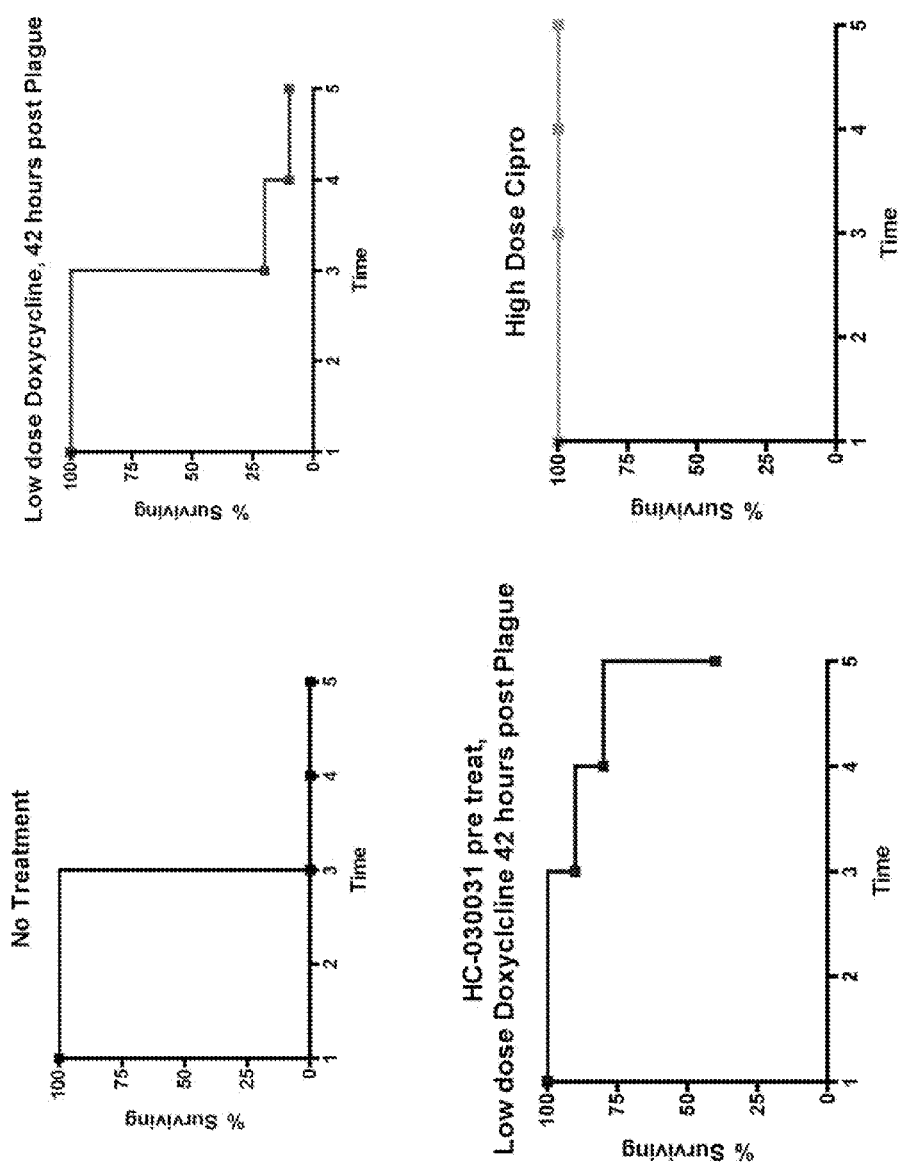

Several research groups are currently evaluating multiple chemotypes for potent TRPA1 antagonists. Selected TRPA1 antagonists are shown in FIG. 2 and discussed below.

From a screen of over 40,000 compounds, Patapoutian and colleagues recently identified AP18 (36), a low molecular weight oxime, as a potent TRPA1 antagonist. Petrus, M.; Peier, A. M.; Bandell, M.; Hwang, S. W.; Huynh, T.; Olney, N.; Jegla, T.; Patapoutian, A. (2007) A role of TRPA1 in mechanical hyperalgesia is revealed by pharmacological inhibition. *Mol Pain* 8:1-8; and Patapoutian, A., International Patent Application Publication No. WO 2007/098252, which is hereby incorporated by reference in its entirety and particularly incorporated by reference for the TRPA1 antagonists described therein. AP18 (36) blocks CA (3) activation of TRPA1 with an $IC_{50}$ of 3.1 µM and 4.5 µM for human and mouse TRPA1, respectively. Further, AP18 (36) is selective for modulation of TRPA1 with respect to TRPV1 to TRPV4 and TRPM8. AP18 (36) has been validated as a useful tool compound in animal studies. For instance, local administration of AP18 (36) significantly reduces nociceptive behaviour caused by complete Freund's adjuvant (CFA) (3) injection in mice as well as the development of CFA-induced mechanical hyperalgesia. Petrus, M. et al., supra. AP18 (36) was without effect in TRPA1 knockout mice, revealing on-target activity. In addition, local administration of AP18 (36) reverses CFA-induced cold allodynia in rats.

Abbott has presented data on A-967079 (37) (Reilly, R. TRPA1 as a pain target: Challenges and progress, *Ion Channels as Therapeutic Targets Conference*, Nov. 3, 2009, NJ, U.S.A), a closely related analog of AP18 (36), that is featured in a recently published patent application (Perner, R. J., International Patent Application Publication No. WO 2009/089082, which is hereby incorporated by reference in its entirety and particularly incorporated by reference for the TRPA1 antagonists described therein; and Perner, R. J., International Patent Application Publication No. WO 2009/089083, which is hereby incorporated by reference in its entirety and particularly incorporated by reference for the TRPA1 antagonists described therein). A-967079 (37) was reported to block AITC induced activation of human TRPA1 in a FLIPR assay with an $IC_{50}$ of 74 nM. Similar potency for inhibition of rat and human TRPA1 in the patch clamp assay has also been reported. It appears that minor structural modification of AP (36) to A-967079 (37) results in over 100-fold improvement in human potency and greater than 20-fold for rat. A-967079 (37) is reported to show over 1000-fold selectivity with respect to TRPV1, TRPV4 and TRPM8, and several-fold selectivity for many additional protein targets. In addition, A-967079 (37) was efficacious in several pain models including a rat knee joint model ($ED_{50}$=112 µmol/kg or 23 mg/kg). The stereochemistry of the oxime double bond (E,E-isomer) in A-967079 (37) is critical for TRPA1 activity since the E,Z-isomer (38) was found to be several-fold less active ($IC_{50}$=701 nM) according to their patent application. Renovis' recent publication outlines SAR around AP 18 (36) and related analogs and reported that a demethylated analog (39, $EC_{50}$=9.4 µM) of AP18 is an agonist for TRPA1. Defalco, J.; Steiger, D.; Gustafson, A.; Emerling, D. E.; Kelly, M. G.; Duncton, M. A. (2010) Oxime derivatives related to AP18: Agonists and antagonists of the TRPA1 receptor. *Bioorg. Med. Chem. Lett.* 20:276-279.

Hydra Biosciences identified a TRPA1 antagonist, HC-030031 (40), from a diverse small molecule library screen. McNamara, C. R.; Mandel-Brehm, J.; Bautista, D. M.; Siemens, J.; Deranian, K. L.; Zhao, M.; Hayward, N. J.; Chong, J. A.; Julius, D.; Moran, M. M.; Fanger, C. M. (2007) TRPA1 mediates formalin-induced pain. *Proc. Natl. Acad. Sci. U.S.A.* 104:13525-13530. HC-030031 (40) blocks activation of heterologously-expressed human TRPA1 by AITC (4) in both $Ca^{2+}$ influx and patch clamp assays with $IC_{50}$ values of 6.2 µM and 0.7 µM, respectively. HC-030031 (40) also blocks formaldehyde activation of the channel with similar potencies ($IC_{50}$=5.3 µM and 1.2 µM for $Ca^{2+}$-influx and patch clamp, respectively). Additionally, in cultured rat DRG cells, HC-030031 (40) blocks increases in intracellular calcium concentration evoked by AITC (4) or formaldehyde. Furthermore, HC-030031 (40) is selective for TRPA1, as it does not block the currents mediated by human TRPV1, TRPV3, TRPV4, hERG and NaV1.2 in patch clamp experiments. The efficacy of HC-030031 (40) for inhibiting TRPA1 activity has been demonstrated in multiple pain models. In the rat formalin pain model, intraperitoneal (i.p.) administration of HC-030031 (40) dose-dependently reduces the number of flinches in both phase I and IIa components of the model. Similarly, AITC (4)-induced flinching in rats is significantly reduced by 300 mg/kg i.p. administration of HC-030031 (40). Merck has reported oral efficacy for HC-030031 (40) in rat models of inflammatory and neuropathic pain as well as in response to injection of CA (3) or AITC (4). Eid, S. R.; Crown, E. D.; Moore, E. L.; Liang, H. A.; Choong, K. C.; Dima, S.; Henze, D. A.; Kane, S. A.; Urban, M. O. (2008) HC-030031, a TRPA1 selective antagonist, attenuates inflammatory- and neuropathy-induced mechanical hypersensitivity. *Mol Pain* 4:48. Oral administration of 100 mg/kg HC-030031 (40) results in 28% reversal of mechanical hypersensitivity in the CFA-induced inflammatory pain model. In the spinal nerve ligation (SNL) model, oral administration of 100 and 300 mg/kg of HC-030031 (40) yields 24% and 45% reversal of mechanical hypersensitivity, respectively.

Other recent studies utilizing HC-030031 (40) have demonstrated a role for TRPA1 in airway physiology. Asthma is an inflammatory disorder that can be triggered by exposure to allergens and chemical irritants (Caceres, A. I.; Brackmann, M.; Elia, M. D.; Bessac, B. F.; del Camino, D.; D'Amours, M.; Witek, J. S.; Fanger, C. M.; Chong, J. A.; Hayward, N. J.; Homer, R. J.; Cohn, L.; Huang, X.; Moran, M. M.; Jordt, S. E. (2009) A sensory neuronal ion channel essential for airway inflammation and hyperreactivity in asthma. *Proc. Natl. Acad. Sci. U.S.A.* 106:9099-9104), and inhibition of TRPA1 may alleviate asthma symptoms. In the murine ovalbumin model of asthma, i.p. administration of 200 mg/kg of HC-030031 (40) per day for 4 days during the ovalbumin challenge resulted in complete suppression of airway hyperreactivity. Recently, TRPA1 agonists such as CA (3) and AITC (4) have been shown to provoke cough in guinea pigs in a dose-dependent manner (Andre, E.; Gatti, R.; Trevisani, M.; Preti, D.; Baraldi, P. G.; Patacchini, R.; Geppetti, P. (2009) Transient receptor potential ankyrin receptor 1 is a novel target for pro-tussive agents. *Br. J. Pharmacol.* 158:1621-1628), as well as in human subjects (Birrell, M. A.; Belvisi, M. G.; Grace, M.; Sadofsky, L.; Faruqi, S.; Hele, D. J.; Maher, S. A.; Freund-Michel, V.; Morice, A. H. (2009) TRPA1 agonists evoke coughing in guinea pig and human volunteers. *Am. J. Respir. Crit. Care Med.* 180:1042-1047. The pro-tussive effects of TRPA1 agonists in guinea pigs are inhibited by HC-030031 (40). Together, these findings suggest that TRPA1 may also be a promising target for the development of anti-asthma and anti-tussive agents.

The TRPA1 antagonist CHEM (41), an analog of HC-030031 (40), has been reported to prevent development of diabetic hypersensitivity in rats. Wei, H.; Ha, M. M.; Pertovaara, A. (2009) Attenuation of Mechanical Hypersensitivity by an Antagonist of the TRPA1 Ion Channel in Diabetic Animals. Anesthesiology 111:147-154. Acute administration of 10 mg/kg of CHEM (41) reduces mechanically induced withdrawal responses in diabetic animals, while administration at 30 mg/kg twice a day for one week results in attenuated development of mechanical hypersensitivity. These results suggest that TRPA1 antagonists may also have potential for treating diabetic disorders.

Three additional HC-030031-related analogs (42-45) were disclosed in various patent applications as potent TRPA1 antagonists. Ng, H., International Patent Application Publication No. WO 2009/002933, which is hereby incorporated by reference in its entirety and particularly incorporated by reference for the TRPA1 antagonists described therein; Muthuppalniappan, M., International Patent Application Publication No. WO 2009/118596, which is hereby incorporated by reference in its entirety and particularly incorporated by reference for the TRPA1 antagonists described therein; Chaudhari, S. S., International Patent Application Publication No. WO 2009/144548, which is hereby incorporated by reference in its entirety and particularly incorporated by reference for the TRPA1 antagonists described therein; and Muthuppalniappan, M., International Patent Application Publication No. WO 2010/004390, which is hereby incorporated by reference in its entirety and particularly incorporated by reference for the TRPA1 antagonists described therein. One recent Glenmark patent application disclosed a quinazolinedione derivative (45) as a potent TRPA1 antagonist with $IC_{50}$ value <100 nM. Muthuppalniappan, M. United States Patent Application Publication No. US 2009/0325987, which is hereby incorporated by reference in its entirety and particularly incorporated by reference for the TRPA1 antagonists described therein. This quinazolinedione derivative (45) has been efficacious in multiple pain models. At a recent conference Glenmark reported GRC-17266 (undisclosed structure) as a potent TRPA1 antagonist in $Ca^{2+}$ flux assay ($IC_{50}$=70 nM) that displayed good selectivity over TRPV1 to TRPV4 and TRPM8. Khairatkar, N. Assays & Cellular Targets, IBC Conference, Ion Channel Targets—Sixth Annual Meeting, 2008, San Diego, Calif., USA. GRC-17266 showed 50% oral bioavailability in rats and 70% reversal of mechanical allodynia when dosed at 10 mg/kg in a nerve injury pain model.

A recent patent application from Jansen Pharmaceutica NV disclosed fused 3,4-dihydropyrimidine analogs as potent TRPA1 antagonists. Gijsen, H. J. N., International Patent Application Publication No. WO 2009/147079, which is hereby incorporated by reference in its entirety and particularly incorporated by reference for the TRPA1 antagonists described therein. The dihydropyrimidine derivative (46) is reported to block TRPA1 activation caused by 11H-dibenzo[b,e]azepine-10-carboxylic acid methyl ester in cells expressing human TRPA1. However only the (R)-isomer (47) is reported to be biologically active; the (S)-isomer (48) is reported to be inactive. No data from in vivo studies were disclosed for these 3,4-dihydropyrimidine derivatives. Amgen has reported that trichloro(sulfanyl)ethyl benzamides, such as AMG9090 (49) and AMG2504 (50), block human TRPA1 current elicited by various agonists. Klionsky, L.; Tamir, R.; Gao, B.; Wang, W.; Immke, D. C.; Nishimura, N.; Gavva, N. R. (2007) Species specific pharmacology of Trichloro(sulfanyl)ethyl benzamides as transient receptor potential ankyrin 1 (TRPA1) antagonists. *Mol Pain* 3:39. These compounds block activation of human TRPA1 by AITC and cold in CHO cells in the patch clamp assay. However both of these compounds, AMG 9090 (49) and AMG2504 (50), failed to block activation of rat TRPA1 even at concentrations up to 30 µM, suggesting that the compounds may inhibit the human TRPA1 channel but not that of the rat.

Another recent patent application from Jansen Pharmaceutica NV described tricyclic compounds having TRPA1 receptor agonistic properties. Gijsen, H. J. N., International Patent Application Publication No. WO 2009/071631, which is hereby incorporated by reference in its entirety and particularly incorporated by reference for the TRPA1 antagonists described therein.

Astellas Pharma Inc. has filed a patent application on indoline compounds that are TRPA1 antagonists. Kaku, H., International Patent Application Publication No. WO 2009/123080, corresponding to US Patent Application Publication No. 2011/0009379, each of which is hereby incorporated by reference in its entirety and particularly incorporated by reference for the TRPA1 antagonists described therein.

In certain embodiments, the TRPA1 antagonist used in the methods described herein is a compound selected from the group consisting of all of the TRPA1 antagonists described in the above-referenced references, patent applications and patents, all of which are hereby incorporated by reference in their entireties.

In certain embodiments, the TRPA1 antagonist used in the methods described herein is selected from the TRPA1 antagonists described in U.S. Pat. No. 7,671,061, which is hereby incorporated by reference in its entirety and particularly incorporated by reference for the TRPA1 antagonists described therein and the methods of making the same.

In certain embodiments, the TRPA1 antagonist used in the methods described herein is selected from the TRPA1 antagonists described in US Patent Application Publication No. US 2010/0249154, which is hereby incorporated by reference in its entirety and particularly incorporated by reference for the TRPA1 antagonists described therein and the methods of making the same.

In certain embodiments, the TRPA1 antagonist used in the methods described herein is selected from the TRPA1 antagonists described in International Patent Application Publication Nos. WO 2007/073505, WO 2009/002933 and WO 2010/039289, all three of which are hereby incorporated by reference in their entireties and particularly incorporated by reference for the TRPA1 antagonists described therein and the methods of making the same.

In certain embodiments, the TRPA1 antagonist used in the methods described herein is selected from the TRPA1 antagonists described in International Patent Application Publication No. WO 2010/138879, which is hereby incorporated by reference in its entirety and particularly incorporated by reference for the TRPA1 antagonists described therein and the methods of making the same.

In certain embodiments, the TRPA1 antagonist used in the methods described herein is a compound represented by formula I, or a pharmaceutically acceptable salt thereof:

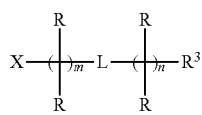
I wherein,

R is hydrogen, $C_1$-$C_6$ alkyl, $C_2$-$C_6$ alkenyl, or $C_2$-$C_6$ alkynyl, halo, hydroxyl, alkoxy, amino, alkylamino, thiol, alkylthiol, nitro, or cyano, each of which is optionally substituted with one or two $R^{11}$;

X is

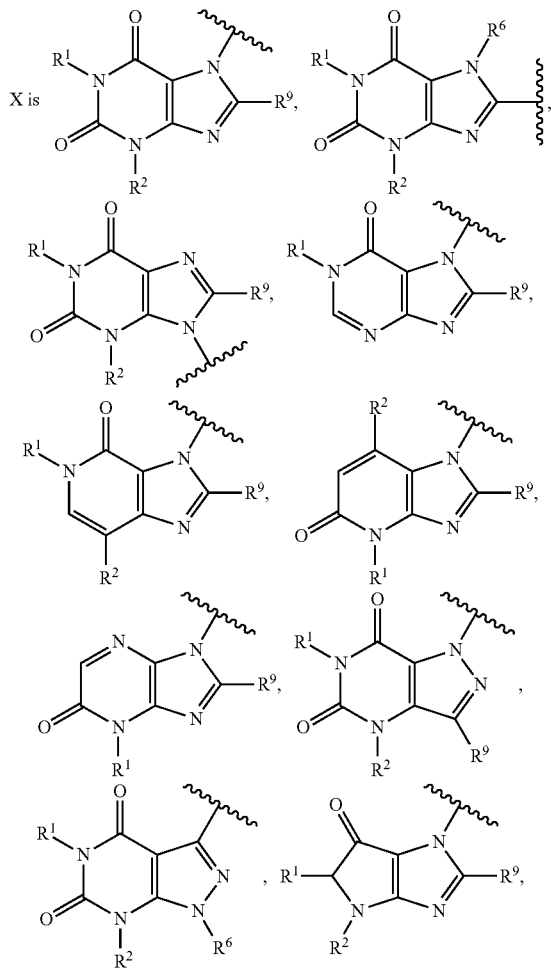

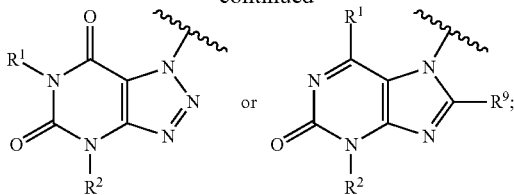

$R^1$ and $R^2$ are each independently hydrogen, $C_1$-$C_6$ alkyl, $C_2$-$C_6$ alkenyl or $C_2$-$C_6$ alkynyl, each of which is optionally substituted with one to four $R^5$;

L is $NR^6SO_2$, $SO_2NR^6$, $C(O)NR^6$, $NR^6C(O)$, $C(S)NR^6$, $NR^6C(S)$, $OC(O)NR^6$, $NR^6C(O)O$, $NR^6C(O)NR^6$, S, S(O), $S(O)_2$, $NR^6$, $CH_2$, O, C(O), $C(O)NR^6SO_2$, $SO_2NR^6C(O)$, heteroarylene or carbocyclylene;

$R^3$ is carbocyclyl, heterocyclyl, aryl, heteroaryl or $R^{3a}$, each of which is optionally substituted with one to four $R^7$;

$R^{3a}$ is carbocyclylene, heterocyclylene, arylene or heteroarylene, each of which is substituted with one $R^{3b}$;

$R^{3b}$ is carbocyclyl, heterocyclyl, aryl or heteroaryl, each of which is optionally substituted with one to four $R^7$;

each $R^5$ is independently halo, hydroxyl, alkoxy, amino, alkylamino, dialkylamino, cyano, nitro, amido, alkylamido, dialkylamido, thioyl, sulfonyl, carbocyclyl, heterocyclyl, aryl or heteroaryl;

each $R^6$ is independently hydrogen, $C_1$-$C_6$ alkyl, $C_1$-$C_6$ alkenyl, hydroxy-$C_1$-$C_6$ alkyl, alkoxy-$C_1$-$C_6$ alkyl, cyanoalkyl, haloalkyl, arylalkyl, —S(O)alkyl, acyl, amino, amidyl, —S(O)H, —S(O)$_2$H, —S(O)$_2$OH, aryl or alkoxyaryl;

each $R^7$ is independently $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, carbocyclyl, heterocyclyl, aryl, heteroaryl, carbocyclylalkyl, heterocyclylalkyl, arylalkyl, heteroarylalkyl, halo, hydroxyl, alkoxy, aryloxy, arylalkoxy, amino, alkylamino, dialkylamino, thioyl, alkylthioyl, sulfonyl, sulfonamidyl (e.g., where the nitrogen of the sulfonamide is substituted with an alkyl, or where the nitrogen of the sulfonamide together with two carbons to which it is attached, forms a heterocycyl), amido (e.g., where the nitrogen of the amide is substituted with an alkyl, or where the nitrogen of the amide together with two carbons to which it is attached, forms a heterocycyl), urea, sulfonylurea, acyl, —C(O)aryl, —NHC(O)aryl, —C(O)NHaryl, —C(O)OH, —C(O)Oalkyl, nitro or cyano, each of which is optionally substituted with one to three $R^8$;

each $R^8$ is independently $C_1$-$C_6$ alkyl, $C_2$-$C_6$ alkenyl, or $C_2$-$C_6$ alkynyl, halo, $C_1$-$C_6$ haloalkyl, hydroxyl, alkoxy, aryloxy, amino, alkylamino, dialkylamino, thioyl, sulfonyl, sulfonamidyl, amido, —C(O)OH, —C(O)Oalkyl, urea, sulfonylurea acyl, nitro, cyano, carbocyclyl, heterocyclyl, aryl, or heteroaryl, each of which is optionally substituted with one to three $C_1$-$C_6$ alkyl, $C_1$-$C_6$ haloalkyl or halo;

$R^9$ is independently hydrogen, $C_1$-$C_6$ alkyl, $C_2$-$C_6$ alkenyl, $C_2$-$C_6$ alkynyl, halo, $C_1$-$C_6$ haloalkyl, hydroxyl, alkoxy, aryloxy, arylalkoxy, amino, alkylamino, dialkylamino, thioyl, alkylthioyl, sulfonyl, sulfonamidyl, amido, urea, sulfonylurea, acyl, nitro or cyano, each of which is optionally substituted with one to three $R^8$;

each $R^{11}$ is independently $C_1$-$C_6$ alkyl, $C_2$-$C_6$ alkenyl, or $C_2$-$C_6$ alkynyl, aryl, heteroaryl, cyclyl, halo, hydroxyl, alkoxy, oxo, aryloxy, amino, alkylamino, dialkylamino, C(O)OH, —C(O)Oalkyl, thioyl, sulfonyl, sulfonamidyl, amido, urea, sulfonylurea, acyl, nitro, cyano, cyclyl, heterocyclyl, aryl, or heteroaryl; and each m and n are independently 0, 1, 2, 3, 4, 5 or 6.

In certain embodiments, the invention relates to any one of the aforementioned compounds and attendant definitions, wherein X is

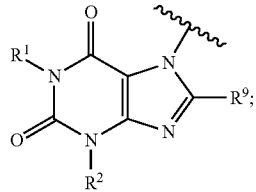

R is hydrogen; L is heteroarylene or cyclopropylene; and n is 1, 2, 3, 4, 5 or 6.

In certain embodiments, the invention relates to any one of the aforementioned compounds and attendant definitions, wherein X is

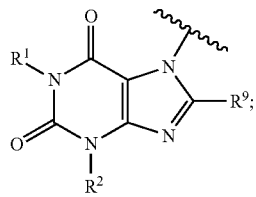

R is hydrogen; L is $NR^6C(O)$ or $C(O)NR^6$; and n is 2, 3, 4, 5 or 6.

In certain embodiments, the invention relates to any one of the aforementioned compounds and attendant definitions, wherein X is

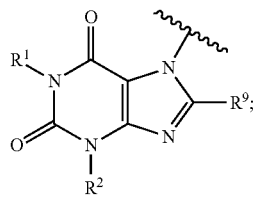

R is hydrogen; L is $NR^6C(O)$ or $C(O)NR^6$; and n is 2, 3, 4, 5 or 6; provided that when m is 1, n is 2, L is C(O)NH, and $R^1$ and $R^2$ are both methyl, $R^3$ is not phenyl.

In certain embodiments, the invention relates to any one of the aforementioned compounds and attendant definitions, wherein X is

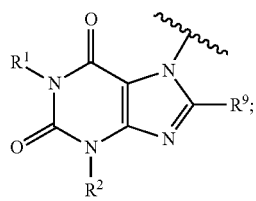

R is hydrogen; L is $NR^6C(O)$ or $C(O)NR^6$; n is 2, 3, 4, 5 or 6; m is 2, 3, 4, 5 or 6.

In certain embodiments, the invention relates to any one of the aforementioned compounds and attendant definitions, wherein X is

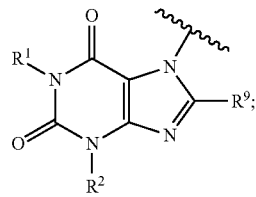

R is hydrogen; L is $NR^6C(O)$ or $C(O)NR^6$; $R^6$ is hydrogen, $C_1$-$C_6$ alkyl, arylalkyl, —S(O)alkyl, acetyl, —S(O)H, —S(O)$_2$H or —S(O)$_2$OH; and n is 0.

In certain embodiments, the invention relates to any one of the aforementioned compounds and attendant definitions, wherein X is

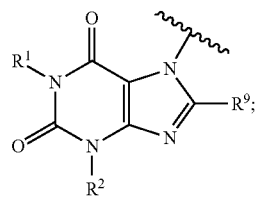

R is hydrogen; L is $C(O)NR^6$; $R^6$ is hydrogen, $C_1$-$C_6$ alkyl, arylalkyl, —S(O)alkyl, acetyl, —S(O)H, —S(O)$_2$H or —S(O)$_2$OH; and n is 0.

In certain embodiments, the invention relates to any one of the aforementioned compounds and attendant definitions, wherein X is

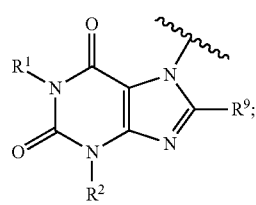

R is hydrogen; L is $NR^6C(O)$; $R^6$ is hydrogen, $C_1$-$C_6$ alkyl, arylalkyl, —S(O)alkyl, acetyl, —S(O)H, —S(O)$_2$H or —S(O)$_2$OH; n is 0; and m is 2, 3, 4, 5 or 6.

In certain embodiments, the invention relates to any one of the aforementioned compounds and attendant definitions, wherein X is

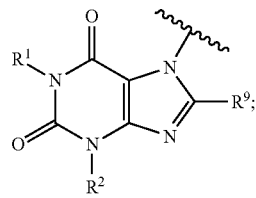

R is hydrogen; L is $NR^6$, $CH_2$ or O; $R^6$ is hydrogen, $C_1$-$C_6$ alkyl, arylalkyl, —S(O)alkyl, acetyl, —S(O)H, —S(O)$_2$H or —S(O)$_2$OH; m is 1, 2, 3, 4, 5 or 6; and n is 1, 2, 3, 4, 5 or 6.

In certain embodiments, the invention relates to any one of the aforementioned compounds and attendant definitions, wherein X is

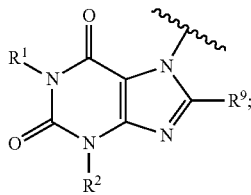

R is hydrogen; L is $NR^6$ or O; $R^6$ is hydrogen, $C_1$-$C_6$ alkyl, arylalkyl, —S(O)alkyl, acetyl, —S(O)H, —S(O)$_2$H or —S(O)$_2$OH; m is 1, 2, 3, 4, 5 or 6; and n is 1, 2, 3, 4, 5 or 6.

In certain embodiments, the invention relates to any one of the aforementioned compounds and attendant definitions, wherein X is

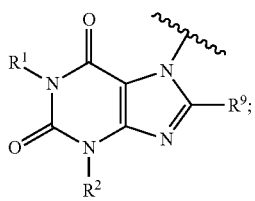

R is hydrogen; L is $CH_2$; $R^6$ is hydrogen, $C_1$-$C_6$ alkyl, arylalkyl, —S(O)alkyl, acetyl, —S(O)H, —S(O)$_2$H or —S(O)$_2$OH; m is 2, 3, 4, 5 or 6; n is 2, 3, 4, 5 or 6; and $R^3$ is phenyl.

In certain embodiments, the invention relates to any one of the aforementioned compounds and attendant definitions, wherein X is

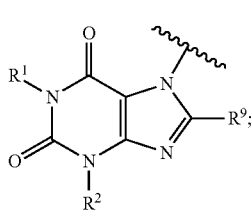

R is hydrogen; L is $CH_2$ or O; $R^6$ is hydrogen, $C_1$-$C_6$ alkyl, arylalkyl, —S(O)alkyl, acetyl, —S(O)H, —S(O)$_2$H or —S(O)$_2$OH; m is 1, 2, 3, 4, 5 or 6; and n is 1, 2, 3, 4, 5 or 6.

In certain embodiments, the invention relates to any one of the aforementioned compounds and attendant definitions, wherein X is

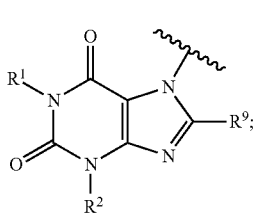

R is hydrogen; L is $NR^6$; $R^6$ is hydrogen, $C_1$-$C_6$ alkyl, arylalkyl, —S(O)alkyl, acetyl, —S(O)H, —S(O)$_2$H or —S(O)$_2$OH; m is 1, 2, 3, 4, 5 or 6; and n is 1, 2, 3, 4, 5 or 6; provided that $R^3$ is not phenyl, methyoxyphenyl or arylcarbonylphenyl.

In certain embodiments, the invention relates to any one of the aforementioned compounds and attendant definitions, wherein X is

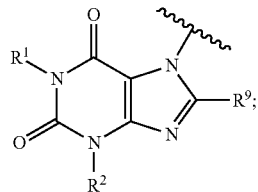

R is hydrogen; L is $NR^6$, $CH_2$ or O; $R^6$ is hydrogen, $C_1$-$C_6$ alkyl, arylalkyl, —S(O)alkyl, acetyl, —S(O)H, —S(O)$_2$H or —S(O)$_2$OH; m is 1, 2, 3, 4, 5 or 6; and n is 1, 2, 3, 4, 5 or 6; provided that when L is $NR^6$ or O, m is not 2.

In certain embodiments, the invention relates to any one of the aforementioned compounds and attendant definitions, wherein X is

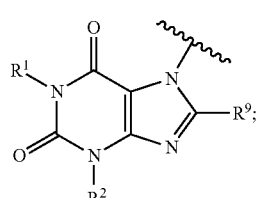

R is hydrogen; $R^1$ is methyl; $R^2$ is methyl; $R^3$ is a 3-membered ring-fused heteroaryl optionally substituted with one to four $R^7$; m is 1; L is $C(O)NR^6$; and n is 0.

In certain embodiments, the invention relates to any one of the aforementioned compounds and attendant definitions, wherein X is

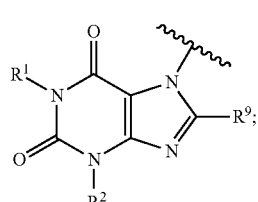

R is hydrogen; $R^1$ is methyl; $R^2$ is methyl; $R^3$ is a 3-membered ring-fused heteroaryl optionally substituted with one, three or four $R^7$; $R^7$ is independently $C_1$-$C_6$ alkyl, $C_2$-$C_6$ alkenyl, $C_2$-$C_6$ alkynyl, halo, hydroyl, alkoxy, acyl, nitro or cyano; m is 1; L is $C(O)NR^6$; and n is 0.

In certain embodiments, the invention relates to any one of the aforementioned compounds and attendant definitions, wherein X is

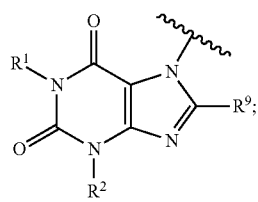

R is hydrogen; R³ is R³ᵃ optionally substituted with one to four R⁷; L is C(O)NR⁶ or CH₂; m is 1; and n is 0.

In certain embodiments, the invention relates to any one of the aforementioned compounds and attendant definitions, wherein X is

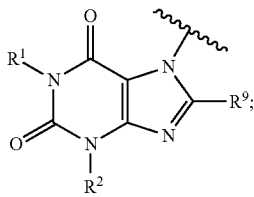

R is hydrogen; R³ is R³ᵃ optionally substituted with one to four R⁷; L is NR⁶SO₂, SO₂NR⁶, C(O)NR⁶, NR⁶C(O), OC(O)NR⁶, NR⁶C(O)O, NR⁶C(O)NR⁶, S, S(O), S(O)₂, NR⁶ or CH₂; m is 2, 3, 4, 5 or 6; and n is 0.

In certain embodiments, the invention relates to any one of the aforementioned compounds and attendant definitions, wherein X is

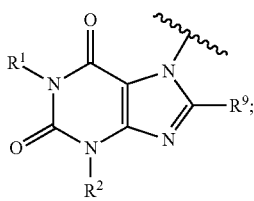

R is hydrogen; R³ is R³ᵃ optionally substituted with one to four R⁷; m is 1, 2, 3, 4, 5 or 6; and n is 0; provided that when L is CH₂, S, C(O)NR⁶ or NR⁶C(O), R³ᵃ is not a 5-membered heterocyclyl, 5-membered heteroaryl or piperazine.

In certain embodiments, the invention relates to any one of the aforementioned compounds and attendant definitions, wherein X is

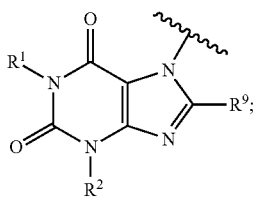

R is hydrogen; R³ is R³ᵃ optionally substituted with one to four R⁷; m is 1, 2, 3, 4, 5 or 6; and n is 0; provided that when L is C(O)NH, R³ᵃ is not phenyl and R³ᵇ is not phenyl.

In certain embodiments, the invention relates to any one of the aforementioned compounds and attendant definitions, wherein X is

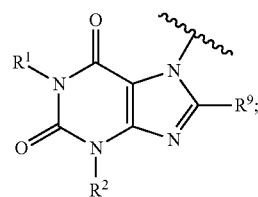

R is hydrogen; R¹ and R² are each independently hydrogen C₁-C₆ alkyl, C₂-C₆ alkenyl, or C₂-C₆ alkynyl, each of which is optionally substituted with one to four R⁵.

In certain embodiments, the invention relates to any one of the aforementioned compounds and attendant definitions, wherein X is

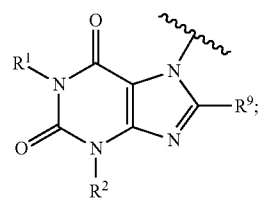

R is hydrogen or C₁-C₄ alkyl; m is 1; L is C(O)NR⁶ or C(S)NR⁶; n is 0; R³ is

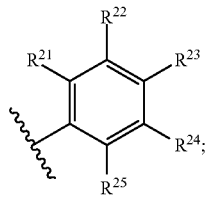

R²¹, R²², R²⁴ and R²⁵ are independently hydrogen or halo; R²³ is —C(R²⁵)₂CF₃, —C(CF₃)=C(R²⁶)₂ or C₃-C₇ cycloalkyl substituted with CF₃; R²⁵ is hydrogen, C₁-C₄ alkyl, fluoro, trifluoromethyl, C₁-C₄ alkoxy or C₁-C₄ haloalkyloxy; and R²⁶ is hydrogen or C₁-C₄ alkyl.

In certain embodiments, the invention relates to any one of the aforementioned compounds and attendant definitions, wherein X is

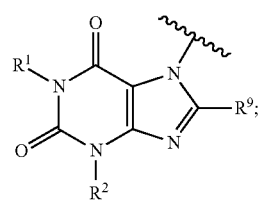

R is hydrogen or C₁-C₄ alkyl; m is 1; L is C(O)NR⁶ or C(S)NR⁶; n is 0; R³ is

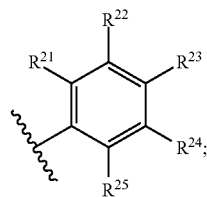

$R^{21}$, $R^{22}$, $R^{24}$ and $R^{25}$ are independently hydrogen, $C_1$-$C_4$ alkyl, halo, cyano, trifluoromethyl, $C_1$-$C_4$ alkoxy, $C_1$-$C_4$ haloalkyloxy, or $C_1$-$C_4$ alkylthio; and $R^{23}$ is trifluoromethyl.

In certain embodiments, the invention relates to any one of the aforementioned compounds and attendant definitions, wherein X is

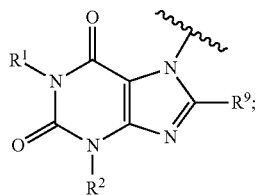

R is hydrogen or $C_1$-$C_4$ alkyl; m is 1; L is $C(O)NR^6$ or $C(S)NR^6$; n is 0; $R^3$ is

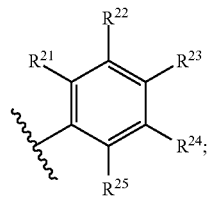

$R^{21}$, $R^{22}$, $R^{23}$ and $R^{25}$ are independently hydrogen, $C_1$-$C_4$ alkyl, halo, cyano, trifluoromethyl, $C_1$-$C_4$ alkoxy, $C_1$-$C_4$ haloalkyloxy, or $C_1$-$C_4$ alkylthio; and $R^{24}$ is trifluoromethyl.

In certain embodiments, the invention relates to any one of the aforementioned compounds and attendant definitions, wherein X is

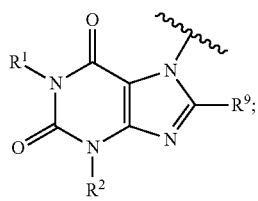

R is hydrogen or $C_1$-$C_4$ alkyl; m is 1; L is $C(O)NR^6$ or $C(S)NR^6$; n is 0; $R^3$ is

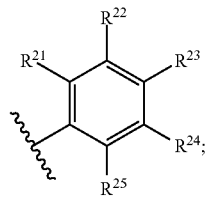

$R^{21}$, $R^{22}$ and $R^{25}$ are independently hydrogen, $C_1$-$C_4$ alkyl, halo, cyano, trifluoromethyl, $C_1$-$C_4$ alkoxy, $C_1$-$C_4$ haloalkyloxy, or $C_1$-$C_4$ alkylthio; $R^{23}$ is hydrogen, $C_2$-$C_4$ alkyl, halo, cyano, trifluoromethyl, $C_1$-$C_4$ alkoxy, $C_1$-$C_4$ haloalkyloxy, or $C_1$-$C_4$ alkylthio; and $R^{24}$ is trifluoromethyl.

In certain embodiments, the invention relates to any one of the aforementioned compounds and attendant definitions, wherein $R^1$ is $C_1$-$C_6$ alkyl.

In certain embodiments, the invention relates to any one of the aforementioned compounds and attendant definitions, wherein $R^1$ is methyl.

In certain embodiments, the invention relates to any one of the aforementioned compounds and attendant definitions, wherein $R^1$ is substituted with one $R^5$; and $R^5$ is dialkyl amine.

In certain embodiments, the invention relates to any one of the aforementioned compounds and attendant definitions, wherein $R^1$ is substituted with one $R^5$; and $R^5$ is dimethyl amine.

In certain embodiments, the invention relates to any one of the aforementioned compounds and attendant definitions, wherein $R^1$ is —$CH_2CH_2N(CH_3)_2$.

In certain embodiments, the invention relates to any one of the aforementioned compounds and attendant definitions, wherein $R^1$ is $C_1$-$C_6$ alkyl substituted with one $R^5$; and $R^5$ is heterocyclyl.

In certain embodiments, the invention relates to any one of the aforementioned compounds and attendant definitions, wherein $R^1$ is $C_1$-$C_6$ alkyl substituted with one $R^5$; and $R^5$ is a nitrogen containing heterocyclyl.

In certain embodiments, the invention relates to any one of the aforementioned compounds and attendant definitions, wherein $R^1$ is $C_1$-$C_6$ alkyl substituted with one $R^5$; and $R^5$ is morpholinyl.

In certain embodiments, the invention relates to any one of the aforementioned compounds and attendant definitions, wherein $R^2$ is $C_1$-$C_6$ alkyl.

In certain embodiments, the invention relates to any one of the aforementioned compounds and attendant definitions, wherein $R^2$ is methyl.

In certain embodiments, the invention relates to any one of the aforementioned compounds and attendant definitions, wherein $R^2$ is substituted with one $R^5$; and $R^5$ is dialkyl amine.

In certain embodiments, the invention relates to any one of the aforementioned compounds and attendant definitions, wherein $R^2$ is substituted with one $R^5$; and $R^5$ is dimethyl amine.

In certain embodiments, the invention relates to any one of the aforementioned compounds and attendant definitions, wherein $R^2$ is —$CH_2CH_2N(CH_3)_2$.

In certain embodiments, the invention relates to any one of the aforementioned compounds and attendant definitions, wherein $R^2$ is $C_1$-$C_6$ alkyl substituted with one $R^5$; and $R^5$ is heterocycly.

In certain embodiments, the invention relates to any one of the aforementioned compounds and attendant definitions, wherein $R^2$ is $C_1$-$C_6$ alkyl substituted with one $R^5$; and $R^5$ is a nitrogen containing heterocyclyl.

In certain embodiments, the invention relates to any one of the aforementioned compounds and attendant definitions, wherein $R^2$ is $C_1$-$C_6$ alkyl substituted with one $R^5$; and $R^5$ is morpholinyl.

In certain embodiments, the invention relates to any one of the aforementioned compounds and attendant definitions, wherein $R^1$ and $R^2$ are $C_1$-$C_6$ alkyl.

In certain embodiments, the invention relates to any one of the aforementioned compounds and attendant definitions, wherein $R^1$ and $R^2$ are methyl.

In certain embodiments, the invention relates to any one of the aforementioned compounds and attendant definitions, wherein $R^3$ is carbocyclyl, heterocyclyl, aryl or heteroaryl, each of which is optionally substituted with one to four $R^7$.

In certain embodiments, the invention relates to any one of the aforementioned compounds and attendant definitions, wherein $R^3$ is monocyclic.

In certain embodiments, the invention relates to any one of the aforementioned compounds and attendant definitions, wherein $R^3$ is a monocyclic carbocyclyl, a monocyclic aryl, a monocyclic heterocyclyl, or a monocyclic heteroaryl.

In certain embodiments, the invention relates to any one of the aforementioned compounds and attendant definitions, wherein $R^3$ is aryl.

In certain embodiments, the invention relates to any one of the aforementioned compounds and attendant definitions, wherein $R^3$ is phenyl. In certain embodiments, the invention relates to any one of the aforementioned compounds and attendant definitions, wherein $R^3$ is phenyl substituted with one to three $R^7$. In certain embodiments, the invention relates to any one of the aforementioned compounds and attendant definitions, wherein $R^3$ is phenyl substituted with one to three $R^7$; and at least one $R^7$ is positioned in the para position. In certain embodiments, the invention relates to any one of the aforementioned compounds and attendant definitions, wherein $R^3$ is phenyl substituted with one $R^7$. In certain embodiments, the invention relates to any one of the aforementioned compounds and attendant definitions, wherein $R^3$ is phenyl substituted with one $R^7$; and $R^7$ is positioned in the para position.

In certain embodiments, the invention relates to any one of the aforementioned compounds and attendant definitions, wherein $R^3$ is 4-methylphenyl.

In certain embodiments, the invention relates to any one of the aforementioned compounds and attendant definitions, wherein $R^3$ is heterocyclyl. In certain embodiments, the invention relates to any one of the aforementioned compounds and attendant definitions, wherein $R^3$ is a nitrogen containing heterocyclyl.

In certain embodiments, the invention relates to any one of the aforementioned compounds and attendant definitions, wherein $R^3$ is a 5-membered heterocyclyl. In certain embodiments, the invention relates to any one of the aforementioned compounds and attendant definitions, wherein $R^3$ is a 5-membered heterocyclyl substituted with one to three $R^7$. In certain embodiments, the invention relates to any one of the aforementioned compounds and attendant definitions, wherein $R^3$ is 5-membered heterocyclyl substituted with one to three $R^7$; and at least one $R^7$ is in the 3-position of the 5-membered ring.

In certain embodiments, the invention relates to any one of the aforementioned compounds and attendant definitions, wherein $R^3$ is a 6-membered heterocyclyl. In certain embodiments, the invention relates to any one of the aforementioned compounds and attendant definitions, wherein $R^3$ is a 6-membered heterocyclyl substituted with one to three $R^7$. In certain embodiments, the invention relates to any one of the aforementioned compounds and attendant definitions, wherein $R^3$ is a 6-membered heterocyclyl substituted with one to three $R^7$; and at least one $R^7$ is in the 4-position of the 6-membered ring.

In certain embodiments, the invention relates to any one of the aforementioned compounds and attendant definitions, wherein $R^3$ is In certain embodiments, the invention relates to any one of the aforementioned compounds and attendant definitions, wherein $R^3$ is heteroaryl. In certain embodiments, the invention relates to any one of the aforementioned compounds and attendant definitions, wherein $R^3$ is a nitrogen-containing heteroaryl.

In certain embodiments, the invention relates to any one of the aforementioned compounds and attendant definitions, wherein $R^3$ is a 5-membered heteroaryl. In certain embodiments, the invention relates to any one of the aforementioned compounds and attendant definitions, wherein $R^3$ is a 5-membered heteroaryl substituted with one to three $R^7$. In certain embodiments, the invention relates to any one of the aforementioned compounds and attendant definitions, wherein $R^3$ is a 5-membered heteroaryl substituted with one to three $R^7$; and at least one $R^7$ is in the 3-position of the 5-membered ring. In certain embodiments, the invention relates to any one of the aforementioned compounds and attendant definitions, wherein $R^3$ is a 5-membered heteroaryl substituted with one to three $R^7$; and at least one $R^7$ is in the 4-position of the 5-membered ring. In certain embodiments, the invention relates to any one of the aforementioned compounds and attendant definitions, wherein $R^3$ is a 5-membered heteroaryl substituted with one $R^7$. In certain embodiments, the invention relates to any one of the aforementioned compounds and attendant definitions, wherein $R^3$ is a 5-membered heteroaryl substituted with one $R^7$; and $R^7$ is in the 3-position of the 5-membered ring. In certain embodiments, the invention relates to any one of the aforementioned compounds and attendant definitions, wherein $R^3$ is a 5-membered heteroaryl substituted with one $R^7$; and $R^7$ is in the 4-position of the 5-membered ring.

In certain embodiments, the invention relates to any one of the aforementioned compounds and attendant definitions, wherein $R^3$ is

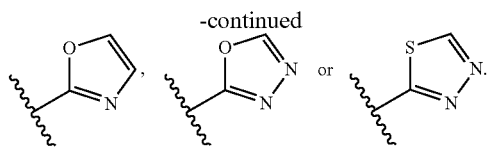

In certain embodiments, the invention relates to any one of the aforementioned compounds and attendant definitions, wherein $R^3$ is a 6-membered heteroaryl. In certain embodiments, the invention relates to any one of the aforementioned compounds and attendant definitions, wherein $R^3$ is a 6-membered heteroaryl substituted with one to three $R^7$. In certain embodiments, the invention relates to any one of the aforementioned compounds and attendant definitions, wherein $R^3$ is a 6-membered heteroaryl substituted with one to three $R^7$; and at least one $R^7$ is positioned in the para position. In certain embodiments, the invention relates to any one of the aforementioned compounds and attendant definitions, wherein $R^3$ is a 6-membered heteroaryl substituted with one $R^7$. In certain embodiments, the invention relates to any one of the aforementioned compounds and attendant definitions, wherein $R^3$ is a 6-membered heteroaryl substituted with one $R^7$; and $R^7$ is positioned in the para position.

In certain embodiments, the invention relates to any one of the aforementioned compounds and attendant definitions, wherein $R^3$ is

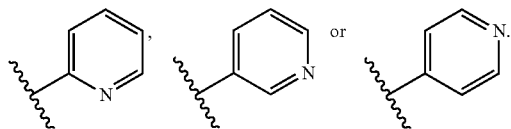

In certain embodiments, the invention relates to any one of the aforementioned compounds and attendant definitions, wherein $R^3$ is a 6-membered heteroaryl containing two nitrogens.

In certain embodiments, the invention relates to any one of the aforementioned compounds and attendant definitions, wherein $R^3$ is

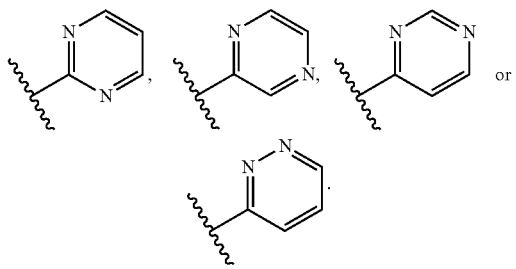

In certain embodiments, the invention relates to any one of the aforementioned compounds and attendant definitions, wherein $R^3$ is a heteroaryl having two fused rings or heterocycyl having two fused rings.

In certain embodiments, the invention relates to any one of the aforementioned compounds and attendant definitions, wherein $R^3$ is a heteroaryl having three fused rings or heterocycyl having three fused rings.

In certain embodiments, the invention relates to any one of the aforementioned compounds and attendant definitions, wherein $R^3$ is $R^{3a}$ optionally substituted with one to four $R^7$.

In certain embodiments, the invention relates to any one of the aforementioned compounds and attendant definitions, wherein $R^{3a}$ is monocyclic.

In certain embodiments, the invention relates to any one of the aforementioned compounds and attendant definitions, wherein $R^{3a}$ is a monocyclic carbocyclylene, a monocyclic arylene, a monocyclic heterocyclylene, or a monocyclic heteroarylene (N.B., "-ylenes" are diradicals, which in the case of $R^{3a}$s have a bond to L and a bond to $R^{3b}$).

In certain embodiments, the invention relates to any one of the aforementioned compounds and attendant definitions, wherein $R^{3a}$ is arylene.

In certain embodiments, the invention relates to any one of the aforementioned compounds and attendant definitions, wherein $R^{3a}$ is phenylene.

In certain embodiments, the invention relates to any one of the aforementioned compounds and attendant definitions, wherein $R^3$ is

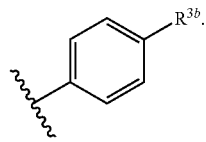

In certain embodiments, the invention relates to any one of the aforementioned compounds and attendant definitions, wherein $R^{3a}$ is heterocyclylene.

In certain embodiments, the invention relates to any one of the aforementioned compounds and attendant definitions, wherein $R^{3a}$ is a 5-membered heterocyclylene. In certain embodiments, the invention relates to any one of the aforementioned compounds and attendant definitions, wherein $R^{3a}$ is a 5-membered heterocyclylene; and $R^{3b}$ is in the 2-position of the 5-membered ring. In certain embodiments, the invention relates to any one of the aforementioned compounds and attendant definitions, wherein $R^{3a}$ is a 5-membered heterocyclylene; and $R^{3b}$ is in the 3-position of the 5-membered ring. In certain embodiments, the invention relates to any one of the aforementioned compounds and attendant definitions, wherein $R^{3a}$ is a 5-membered heterocyclylene; and $R^{3b}$ is in the 4-position of the 5-membered ring. In certain embodiments, the invention relates to any one of the aforementioned compounds and attendant definitions, wherein $R^{3a}$ is a 5-membered heterocyclylene; and $R^{3b}$ is in the 5-position of the 5-membered ring.

In certain embodiments, the invention relates to any one of the aforementioned compounds and attendant definitions, wherein $R^{3a}$ is a 6-membered heterocyclylene. In certain embodiments, the invention relates to any one of the aforementioned compounds and attendant definitions, wherein $R^{3a}$ is a 6-membered heterocyclylene; and $R^{3b}$ is in the 2-position of the 6-membered ring. In certain embodiments, the invention relates to any one of the aforementioned compounds and attendant definitions, wherein $R^{3a}$ is a 6-membered heterocyclylene; and $R^{3b}$ is in the 3-position of the 6-membered ring. In certain embodiments, the invention relates to any one of the aforementioned compounds and attendant definitions, wherein $R^{3a}$ is a 6-membered heterocyclylene; and $R^{3b}$ is in the 4-position of the 6-membered ring. In certain embodiments, the invention relates to any one of the aforementioned compounds and attendant definitions, wherein $R^{3a}$ is a 6-membered heterocyclylene; and $R^{3b}$ is in the 5-position of the 6-membered ring. In certain embodiments, the invention relates to any one of the aforementioned compounds and attendant definitions, wherein $R^{3a}$ is a 6-membered heterocyclylene; and $R^{3b}$ is in the 6-position of the 6-membered ring.

In certain embodiments, the invention relates to any one of the aforementioned compounds and attendant definitions, wherein $R^3$ is

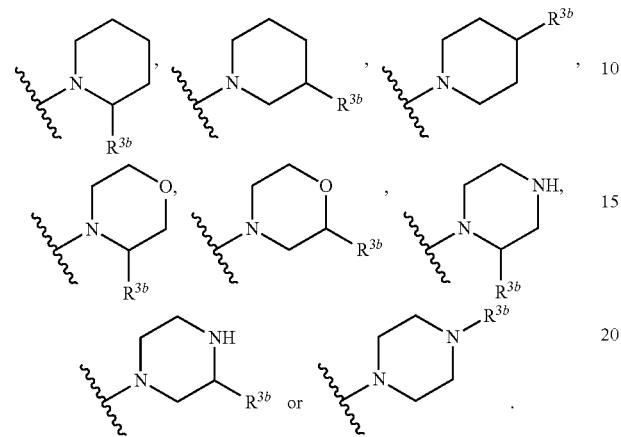

In certain embodiments, the invention relates to any one of the aforementioned compounds and attendant definitions, wherein $R^{3a}$ is heteroarylene.

In certain embodiments, the invention relates to any one of the aforementioned compounds and attendant definitions, wherein $R^{3a}$ is a 5-membered heteroarylene. In certain embodiments, the invention relates to any one of the aforementioned compounds and attendant definitions, wherein $R^{3a}$ is a 5-membered heteroarylene; and $R^{3b}$ is in the 2-position of the 5-membered ring. In certain embodiments, the invention relates to any one of the aforementioned compounds and attendant definitions, wherein $R^{3a}$ is a 5-membered heteroarylene; and $R^{3b}$ is in the 3-position of the 5-membered ring. In certain embodiments, the invention relates to any one of the aforementioned compounds and attendant definitions, wherein $R^{3a}$ is a 5-membered heteroarylene; and $R^{3b}$ is in the 4-position of the 5-membered ring. In certain embodiments, the invention relates to any one of the aforementioned compounds and attendant definitions, wherein $R^{3a}$ is a 5-membered heteroarylene; and $R^{3b}$ is in the 5-position of the 5-membered ring. In certain embodiments, the invention relates to any one of the aforementioned compounds and attendant definitions, wherein $R^{3a}$ is a 5-membered heteroarylene substituted with at least one $R^7$ is in the 2-position of the 5-membered ring. In certain embodiments, the invention relates to any one of the aforementioned compounds and attendant definitions, wherein $R^{3a}$ is a 5-membered heteroarylene substituted with at least one $R^7$ is in the 3-position of the 5-membered ring. In certain embodiments, the invention relates to any one of the aforementioned compounds and attendant definitions, wherein $R^{3a}$ is a 5-membered heteroarylene substituted with at least one $R^7$ is in the 4-position of the 5-membered ring. In certain embodiments, the invention relates to any one of the aforementioned compounds and attendant definitions, wherein $R^{3a}$ is a 5-membered heteroarylene substituted with at least one $R^7$ is in the 5-position of the 5-membered ring.

In certain embodiments, the invention relates to any one of the aforementioned compounds and attendant definitions, wherein $R^3$ is

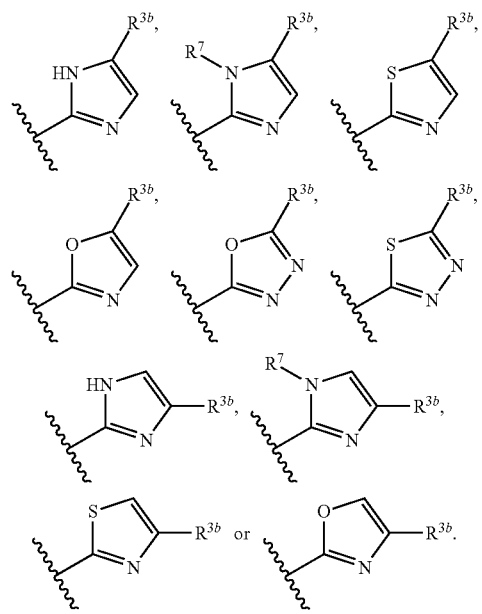

In certain embodiments, the invention relates to any one of the aforementioned compounds and attendant definitions, wherein $R^3$ is

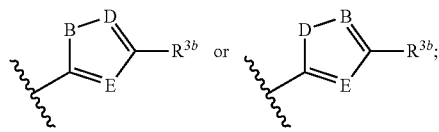

wherein B is O, S or $NR^6$; D is CH, $CR^7$ or N; and E is CH, $CR^7$ or N.

In certain embodiments, the invention relates to any one of the aforementioned compounds and attendant definitions, wherein $R^3$ is

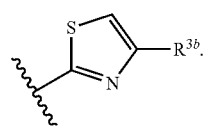

In certain embodiments, the invention relates to any one of the aforementioned compounds and attendant definitions, wherein $R^{3a}$ is

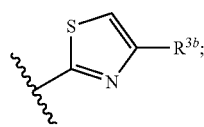

and $R^{3b}$ is phenylene optionally substituted with one to four $R^7$. In certain embodiments, the invention relates to any one of the aforementioned compounds and attendant definitions, wherein $R^3$ is

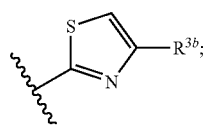

and $R^{3b}$ is phenyl substituted with one to four $R^7$. In certain embodiments, the invention relates to any one of the aforementioned compounds and attendant definitions, wherein $R^3$ is

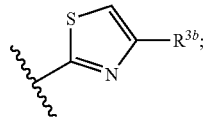

$R^{3b}$ is phenyl substituted with one to four $R^7$; and at least one $R^7$ is amino, alkylamino, dialkylamino or heterocycyl (e.g., a nitrogen containing heterocyclyl such as pyrrolidine or piperidine). In certain embodiments, the invention relates to any one of the aforementioned compounds and attendant definitions, wherein $R^3$ is

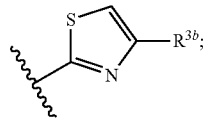

$R^{3b}$ is phenyl substituted with one to four $R^7$; at least one $R^7$ is amino, alkylamino, dialkylamino or heterocycyl (e.g., a nitrogen containing heterocyclyl such as pyrrolidine or piperidine); and the at least one $R^7$ is in the para position.

In certain embodiments, the invention relates to any one of the aforementioned compounds and attendant definitions, wherein $R^{3a}$ is a 6-membered heteroarylene. In certain embodiments, the invention relates to any one of the aforementioned compounds and attendant definitions, wherein $R^{3a}$ is a 6-membered heteroarylene; and $R^{3b}$ is in the 2-position of the 6-membered ring. In certain embodiments, the invention relates to any one of the aforementioned compounds and attendant definitions, wherein $R^{3a}$ is a 6-membered heteroarylene; and $R^{3b}$ is in the 3-position of the 6-membered ring. In certain embodiments, the invention relates to any one of the aforementioned compounds and attendant definitions, wherein $R^{3a}$ is a 6-membered heteroarylene; and $R^{3b}$ is in the 4-position of the 6-membered ring. In certain embodiments, the invention relates to any one of the aforementioned compounds and attendant definitions, wherein $R^{3a}$ is a 6-membered heteroarylene; and $R^{3b}$ is in the 5-position of the 6-membered ring. In certain embodiments, the invention relates to any one of the aforementioned compounds and attendant definitions, wherein $R^{3a}$ is a 6-membered heteroarylene; and $R^{3b}$ is in the 6-position of the 6-membered ring. In certain embodiments, the invention relates to any one of the aforementioned compounds and attendant definitions, wherein $R^{3a}$ is a 6-membered heteroarylene substituted with at least one $R^7$ in the 2-position of the 6-membered ring. In certain embodiments, the invention relates to any one of the aforementioned compounds and attendant definitions, wherein $R^{3a}$ is a 6-membered heteroarylene substituted with at least one $R^7$ in the 3-position of the 6-membered ring. In certain embodiments, the invention relates to any one of the aforementioned compounds and attendant definitions, wherein $R^{3a}$ is a 6-membered heteroarylene substituted with at least one $R^7$ in the 4-position of the 6-membered ring.

In certain embodiments, the invention relates to any one of the aforementioned compounds and attendant definitions, wherein $R^3$ is

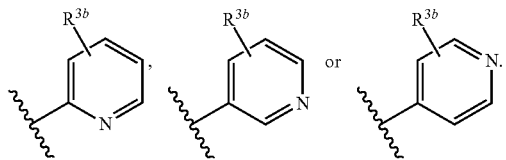

In certain embodiments, the invention relates to any one of the aforementioned compounds and attendant definitions, wherein $R^{3a}$ is a 6-membered heteroarylene containing two nitrogens.

In certain embodiments, the invention relates to any one of the aforementioned compounds and attendant definitions, wherein $R^3$ is

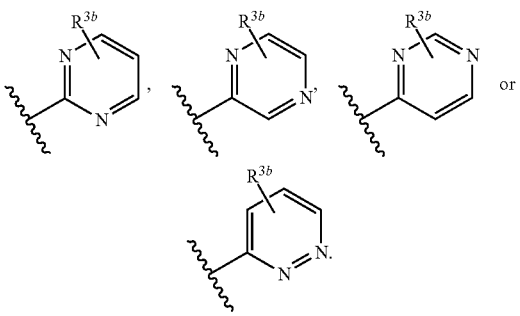

In certain embodiments, the invention relates to any one of the aforementioned compounds and attendant definitions, wherein $R^{3a}$ is a heteroarylene having two fused rings or heterocycylene having two fused rings.

In certain embodiments, the invention relates to any one of the aforementioned compounds and attendant definitions, wherein $R^{3a}$ is a heteroaryl having three fused rings or heterocycyl having three fused rings.

In certain embodiments, the invention relates to any one of the aforementioned compounds and attendant definitions, wherein $R^{3b}$ is phenyl. In certain embodiments, the invention relates to any one of the aforementioned compounds and attendant definitions, wherein $R^{3b}$ is phenyl substituted with one to three $R^7$.

In certain embodiments, the invention relates to any one of the aforementioned compounds and attendant definitions, wherein $R^{3b}$ is a heteroaryl having two fused rings or heterocycyl having two fused rings.

In certain embodiments, the invention relates to any one of the aforementioned compounds and attendant definitions, wherein $R^{3b}$ is phenylene, optionally substituted with one to four $R^7$. In certain embodiments, the invention relates to any one of the aforementioned compounds and attendant definitions, wherein $R^{3b}$ is phenylene, substituted with one to four $R^7$.

In certain embodiments, the invention relates to any one of the aforementioned compounds and attendant definitions, wherein $R^3$ is

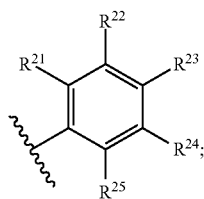

$R^{21}$, $R^{22}$, $R^{24}$ and $R^{25}$ are independently hydrogen or halo; $R^{23}$ is —C($R^{25}$)$_2$CF$_3$, —C(CF$_3$)=C($R^{26}$)$_2$ or C$_3$-C$_7$ cycloalkyl substituted with CF$_3$; $R^{25}$ is hydrogen, C$_1$-C$_4$ alkyl, fluoro, trifluoromethyl, C$_1$-C$_4$ alkoxy or C$_1$-C$_4$ haloalkyloxy; and $R^{26}$ is hydrogen or C$_1$-C$_4$ alkyl.

In certain embodiments, the invention relates to any one of the aforementioned compounds and attendant definitions, wherein $R^3$ is

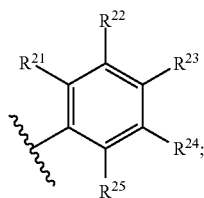

$R^{21}$, $R^{22}$, $R^{24}$ and $R^{25}$ are independently hydrogen, C$_1$-C$_4$ alkyl, halo, cyano, trifluoromethyl, C$_1$-C$_4$ alkoxy, C$_1$-C$_4$ haloalkyloxy, or C$_1$-C$_4$ alkylthio; and $R^{23}$ is trifluoromethyl.

In certain embodiments, the invention relates to any one of the aforementioned compounds and attendant definitions, wherein $R^3$ is

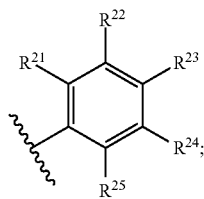

$R^{21}$, $R^{22}$, $R^{23}$ and $R^{25}$ are independently hydrogen, C$_1$-C$_4$ alkyl, halo, cyano, trifluoromethyl, C$_1$-C$_4$ alkoxy, C$_1$-C$_4$ haloalkyloxy, or C$_1$-C$_4$ alkylthio; and $R^{24}$ is trifluoromethyl.

In certain embodiments, the invention relates to any one of the aforementioned compounds and attendant definitions, $R^3$ is

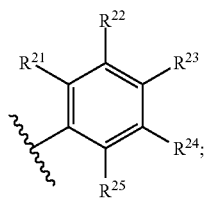

$R^{21}$, $R^{22}$ and $R^{25}$ are independently hydrogen, C$_1$-C$_4$ alkyl, halo, cyano, trifluoromethyl, C$_1$-C$_4$ alkoxy, C$_1$-C$_4$ haloalkyloxy, or C$_1$-C$_4$ alkylthio; $R^{23}$ is hydrogen, C$_2$-C$_4$ alkyl, halo, cyano, trifluoromethyl, C$_1$-C$_4$ alkoxy, C$_1$-C$_4$ haloalkyloxy, or C$_1$-C$_4$ alkylthio; and $R^{24}$ is trifluoromethyl.

In certain embodiments, the invention relates to any one of the aforementioned compounds and attendant definitions, wherein any of the aforementioned $R^3$ is substituted with one $R^7$. In certain embodiments, the invention relates to any one of the aforementioned compounds and attendant definitions, wherein any of the aforementioned $R^3$ is substituted with two $R^7$. In certain embodiments, the invention relates to any one of the aforementioned compounds and attendant definitions, wherein any of the aforementioned $R^3$ is substituted with three $R^7$. In certain embodiments, the invention relates to any one of the aforementioned compounds and attendant definitions, wherein any of the aforementioned $R^3$ is substituted with four $R^7$. In certain embodiments, the invention relates to any one of the aforementioned compounds and attendant definitions, wherein any of the aforementioned R is substituted with one $R^7$; and $R^7$ is methyl, methoxy or halo.

In certain embodiments, the invention relates to any one of the aforementioned compounds and attendant definitions, wherein any of the aforementioned $R^{3a}$ is substituted with one to three $R^7$. In certain embodiments, the invention relates to any one of the aforementioned compounds and attendant definitions, wherein any of the aforementioned $R^{3a}$ is substituted with one to three $R^7$; and $R^7$ is methyl, methoxy or halo. In certain embodiments, the invention relates to any one of the aforementioned compounds and attendant definitions, wherein any of the aforementioned $R^{3a}$ is substituted with one $R^7$. In certain embodiments, the invention relates to any one of the aforementioned compounds and attendant definitions, wherein any of the aforementioned $R^{3a}$ is substituted with one $R^7$; and $R^7$ is methyl, methoxy or halo.

In certain embodiments, the invention relates to any one of the aforementioned compounds and attendant definitions, wherein any of the aforementioned $R^{3b}$ is substituted with one to three $R^7$. In certain embodiments, the invention relates to any one of the aforementioned compounds and attendant definitions, wherein any of the aforementioned $R^{3b}$ is substituted with one to three $R^7$; and $R^7$ is methyl, methoxy or halo. In certain embodiments, the invention relates to any one of the aforementioned compounds and attendant definitions, wherein any of the aforementioned $R^{3b}$ is substituted with one $R^7$. In certain embodiments, the invention relates to any one of the aforementioned compounds and attendant definitions, wherein any of the aforementioned $R^{3b}$ is substituted with one $R^7$; and $R^7$ is methyl, methoxy or halo.

In certain embodiments, the invention relates to any one of the aforementioned compounds and attendant definitions, wherein each $R^7$ is independently C$_1$-C$_6$ alkyl, C$_2$-C$_6$ alkenyl, C$_2$-C$_6$ alkynyl, halo, hydroxyl, alkoxy, aryloxy, arylalkoxy, amino, alkylamino, dialkylamino, thioyl, alkylthioyl, sulfonyl, sulfonamidyl, amido, urea, sulfonylurea, acyl, nitro or cyano, each of which is optionally substituted with one to three $R^8$.

In some embodiments, each $R^7$ is independently C$_1$-C$_6$ alkyl, C$_2$-C$_6$ alkenyl, C$_2$-C$_6$ alkynyl, halo, hydroxyl, alkoxy, oxo, aryl, heteroaryl, carbocyclyl, heterocyclyl, aryloxy, arylalkoxy, amino, alkylamino, dialkylamino, thioyl, alkylthioyl, sulfonyl, sulfonamidyl, amido, urea, sulfonylurea, acyl, nitro, or cyano, each of which is optionally substituted with one to three $R^8$.

In certain embodiments, the invention relates to any one of the aforementioned compounds and attendant definitions, wherein $R^7$ is methyl, methyoxy or halo.

In certain embodiments, the invention relates to any one of the aforementioned compounds and attendant definitions, wherein L is NR$^6$SO$_2$, SO$_2$NR$^6$, C(O)NR$^6$, NR$^6$C(O), OC(O)NR$^6$, NR$^6$C(O)O, NR$^6$C(O)NR$^6$, S, S(O), S(O)$_2$, C(O)NS(O)$_2$, S(O)$_2$NC(O), heteroarylene or carbocyclylene.

In certain embodiments, the invention relates to any one of the aforementioned compounds and attendant definitions, wherein L is $NR^6SO_2$, $SO_2NR^6$, $OC(O)NR_6$, $NR_6C(O)O$, $NR^6C(O)NR^6$, S, S(O), S(O)$_2$, $C(O)NR^6S(O)_2$, $S(O)_2NR^6C(O)$, heteroarylene or carbocyclyl.

In certain embodiments, the invention relates to any one of the aforementioned compounds and attendant definitions, wherein L is $NR^6SO_2$, $SO_2NR^6$, $C(O)NR^6$, $NR^6C(O)$, $OC(O)NR^6$, $NR^6C(O)O$, $NR^6C(O)NR^6$, S, S(O), S(O)$_2$, $NR^6$ or $CH_2$.

In certain embodiments, the invention relates to any one of the aforementioned compounds and attendant definitions, wherein L is $NR^6SO_2$ or $SO_2NR^6$, $OC(O)NR^6$, $NR^6C(O)O$, $NR^6C(O)NR^6$.

In certain embodiments, the invention relates to any one of the aforementioned compounds and attendant definitions, wherein L is $NHSO_2$ or $SO_2NH$, $OC(O)NH$, $NHC(O)O$, $NHC(O)NH$.

In certain embodiments, the invention relates to any one of the aforementioned compounds and attendant definitions, wherein L is $OC(O)NR^6$ or $NR^6C(O)O$.

In certain embodiments, the invention relates to any one of the aforementioned compounds and attendant definitions, wherein L is $OC(O)NH$ or $NHC(O)O$.

In certain embodiments, the invention relates to any one of the aforementioned compounds and attendant definitions, wherein L is $NR^6C(O)NR^6$.

In certain embodiments, the invention relates to any one of the aforementioned compounds and attendant definitions, wherein L is $NHC(O)NH$.

In certain embodiments, the invention relates to any one of the aforementioned compounds and attendant definitions, wherein L is carbocyclylene or heterocyclylene.

In certain embodiments, the invention relates to any one of the aforementioned compounds and attendant definitions, wherein L is cyclopropylene.

In certain embodiments, the invention relates to any one of the aforementioned compounds and attendant definitions, wherein L is C(O).

In certain embodiments, the invention relates to any one of the aforementioned compounds and attendant definitions, wherein $R^9$ is H.

In certain embodiments, the invention relates to any one of the aforementioned compounds and attendant definitions, wherein $R^9$ is halo.

In certain embodiments, the invention relates to any one of the aforementioned compounds and attendant definitions, wherein $R^9$ is chloro.

In certain embodiments, the invention relates to any one of the aforementioned compounds and attendant definitions, wherein m is 0. In certain embodiments, the invention relates to any one of the aforementioned compounds and attendant definitions, wherein m is 1. In certain embodiments, the invention relates to any one of the aforementioned compounds and attendant definitions, wherein m is 2. In certain embodiments, the invention relates to any one of the aforementioned compounds and attendant definitions, wherein m is 3. In certain embodiments, the invention relates to any one of the aforementioned compounds and attendant definitions, wherein m is 4. In certain embodiments, the invention relates to any one of the aforementioned compounds and attendant definitions, wherein m is 5. In certain embodiments, the invention relates to any one of the aforementioned compounds and attendant definitions, wherein m is 6.

In certain embodiments, the invention relates to any one of the aforementioned compounds and attendant definitions, wherein n is 0. In certain embodiments, the invention relates to any one of the aforementioned compounds and attendant definitions, wherein n is 1. In certain embodiments, the invention relates to any one of the aforementioned compounds and attendant definitions, wherein n is 2. In certain embodiments, the invention relates to any one of the aforementioned compounds and attendant definitions, wherein n is 3. In certain embodiments, the invention relates to any one of the aforementioned compounds and attendant definitions, wherein n is 4. In certain embodiments, the invention relates to any one of the aforementioned compounds and attendant definitions, wherein n is 5. In certain embodiments, the invention relates to any one of the aforementioned compounds and attendant definitions, wherein n is 6.

In certain embodiments, the invention relates to any one of the aforementioned compounds and attendant definitions, wherein m is 1; and n is 2. In certain embodiments, the invention relates to any one of the aforementioned compounds and attendant definitions, wherein $R^1$ is methyl; $R^2$ is methyl; m is 1; and n is 2. In certain embodiments, the invention relates to any one of the aforementioned compounds and attendant definitions, wherein $R^1$ is methyl; $R^2$ is methyl; L is C(O)NH; m is 1; and n is 2.

In certain embodiments, the invention relates to any one of the aforementioned compounds and attendant definitions, wherein m is 1; and n is 0. In certain embodiments, the invention relates to any one of the aforementioned compounds and attendant definitions, wherein $R^1$ is methyl; $R^2$ is methyl; m is 1; and n is 0.

In certain embodiments, the invention relates to any one of the aforementioned compounds and attendant definitions, wherein m+n≤6.

In certain embodiments, the invention relates to any one of the aforementioned compounds and attendant definitions, wherein R is hydrogen; X is

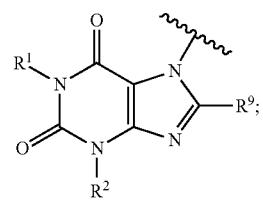

$R^1$ is methyl; $R^2$ is methyl; $R^9$ is methyl; m is 1; L is C(O)NH; and $R^3$ is aryl substituted with one to four $R^7$.

In certain embodiments, the invention relates to any one of the aforementioned compounds and attendant definitions, wherein R is hydrogen; X is

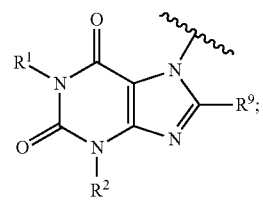

$R^1$ is methyl; $R^2$ is methyl; $R^9$ is methyl; m is 1; L is C(O)NH; and $R^3$ is phenyl substituted with one to three $R^7$.

In certain embodiments, the invention relates to any one of the aforementioned compounds and attendant definitions, wherein R is hydrogen; X is

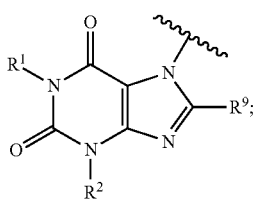

$R^1$ is methyl; $R^2$ is methyl; $R^9$ is methyl; m is 1; L is C(O)NH; and $R^3$ is phenyl substituted in the meta and/or para position with one to three $R^7$.

In certain embodiments, the invention relates to any one of the aforementioned compounds and attendant definitions, wherein R is hydrogen; X is

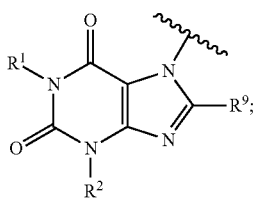

$R^1$ is methyl; $R^2$ is methyl; $R^9$ is methyl; m is 1; L is C(O)NH; $R^3$ is phenyl substituted in the meta and/or para position with one to three $R^7$; and each $R^7$ is independently selected from the group consisting of

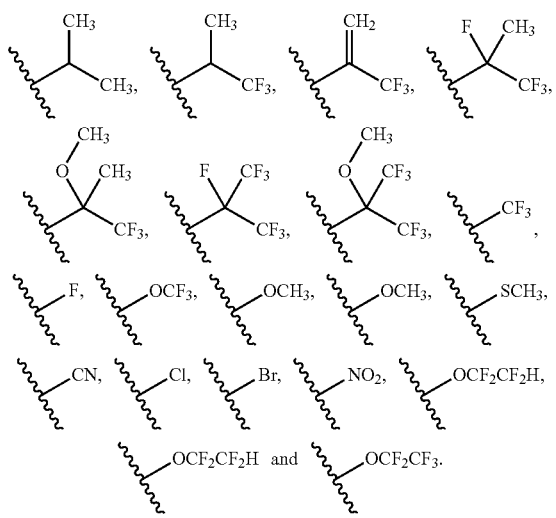

In certain embodiments, the TRPA1 antagonist used in the methods described herein is selected from the group consisting of compounds of formula I and pharmaceutically acceptable salts thereof compounds of formula II and pharmaceutically acceptable salts thereof; TRPA1 antagonists as described in International Patent Application Publication Nos. WO 2007/098252, WO 2009/089082, WO 2009/089083, WO 2009/002933, WO 2009/118596, WO 2009/144548, WO 2010/004390, WO 2009/147079, WO 2009/071631, WO 2009/123080, WO 2007/073505, WO 2010/039289, and WO 2010/138879, and pharmaceutically acceptable salts thereof; TRPA1 antagonists as described in United States Patent Application Publication Nos. 2009/0325987 and 2010/0249154, and pharmaceutically acceptable salts thereof and TRPA1 antagonists as described in U.S. Pat. No. 7,671,061, and pharmaceutically acceptable salts thereof.

In certain embodiments, the TRPA1 antagonist used in the methods described herein is selected from the group consisting of compounds of formula I and pharmaceutically acceptable salts thereof and compounds of formula II and pharmaceutically acceptable salts thereof.

In certain embodiments, the TRPA1 antagonist used in the methods described herein is selected from the group consisting

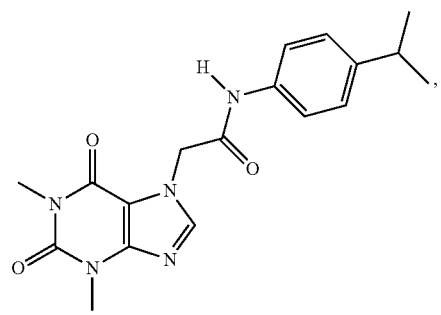

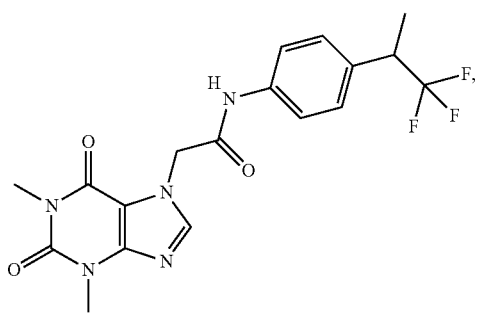

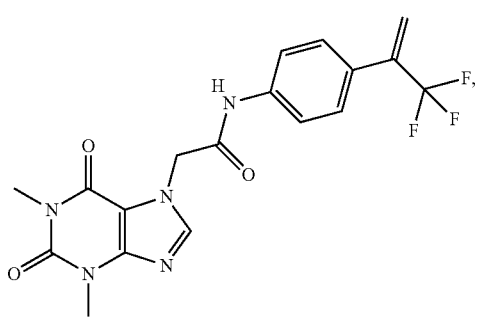

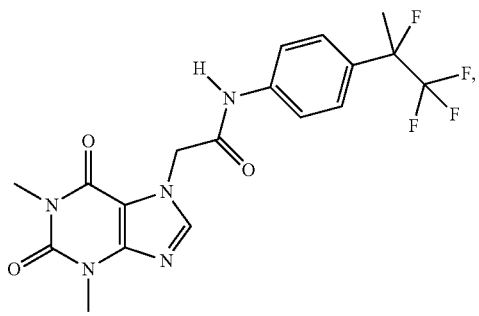

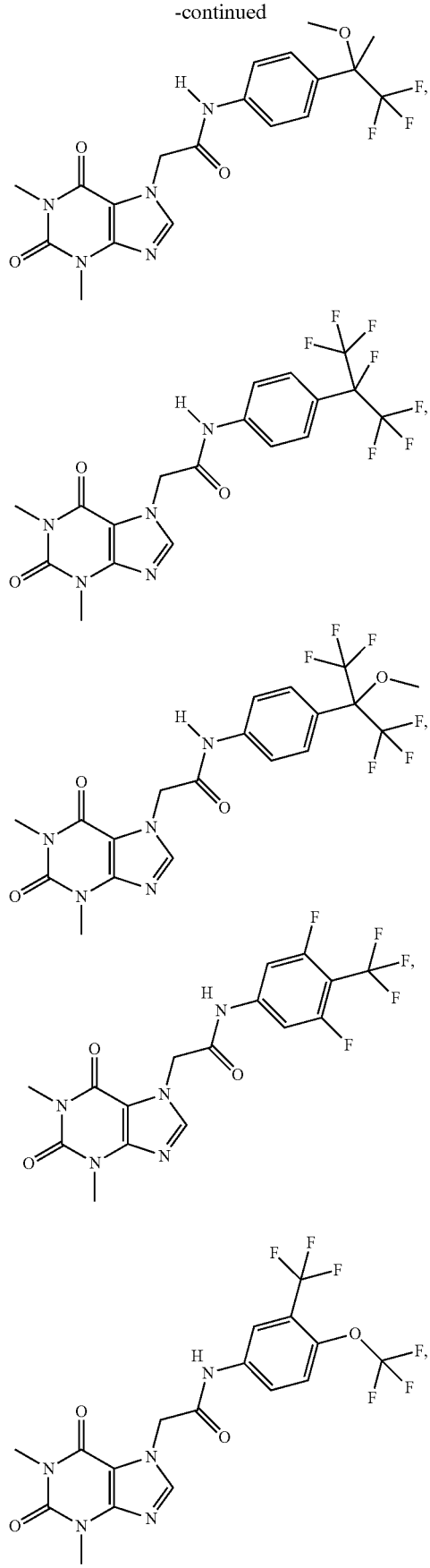
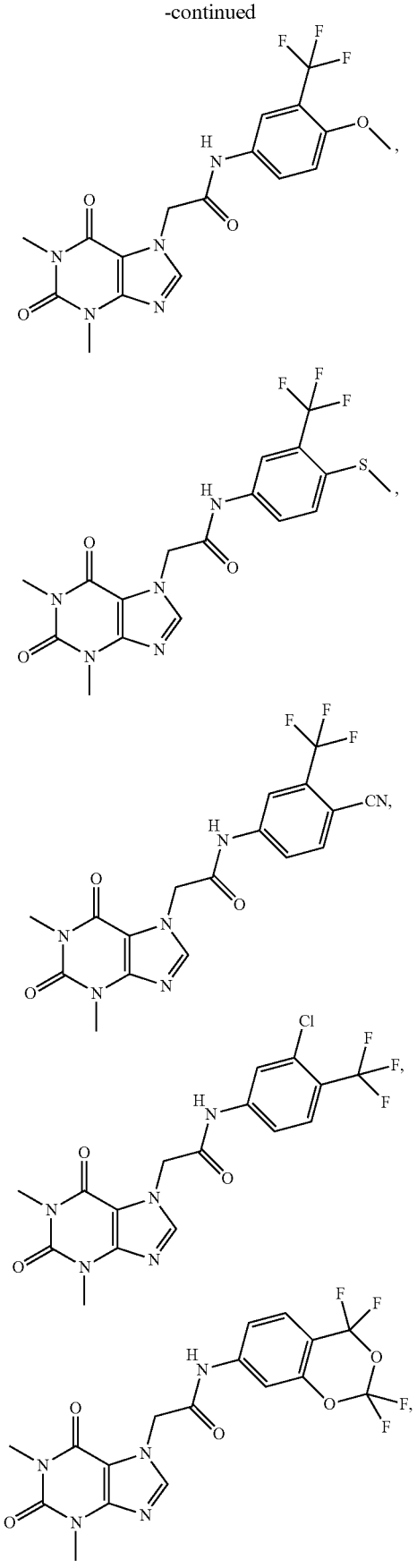

-continued

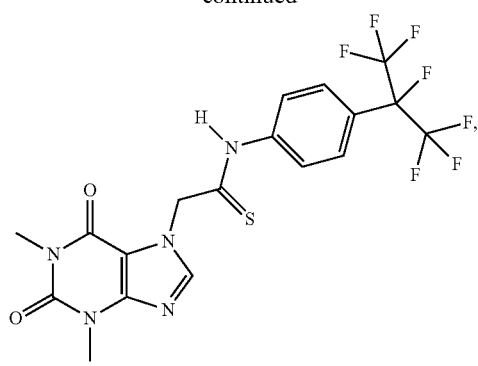

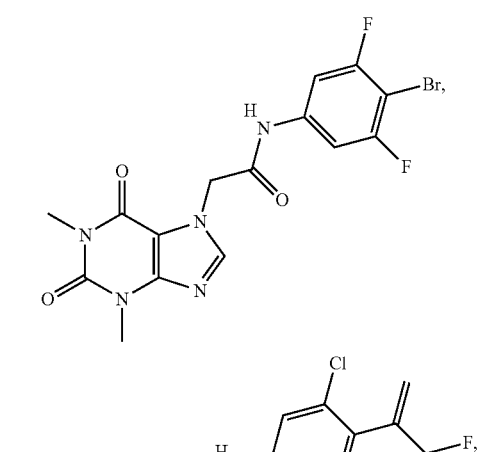

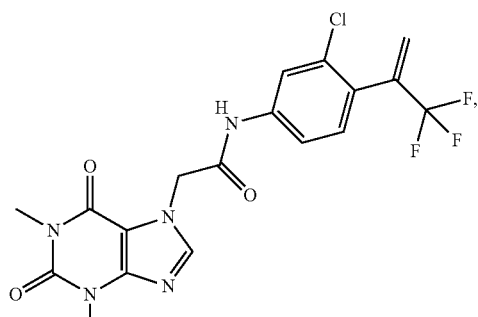

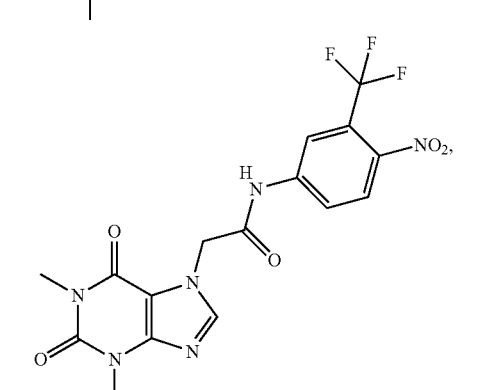

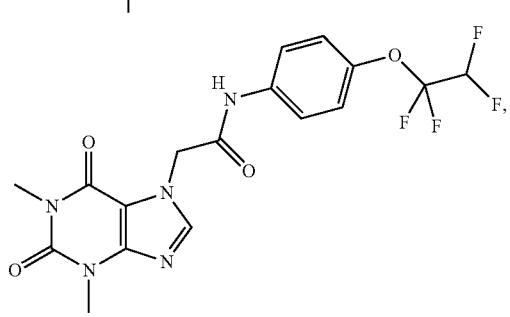

-continued

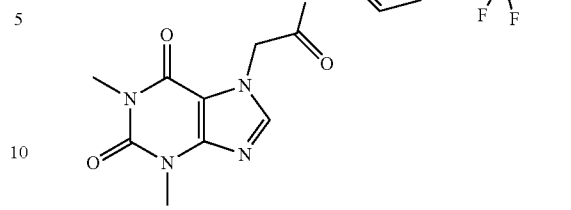

and pharmaceutically acceptable salts thereof.

In certain embodiments, the TRPA1 antagonist used in the methods described herein is selected from the group consisting of

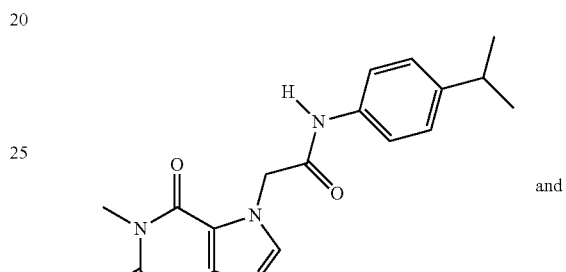

and

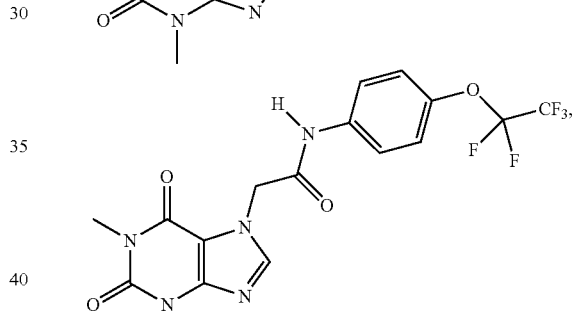

and pharmaceutically acceptable salts thereof.

In certain embodiments, the TRPA1 antagonist used in the methods described herein is

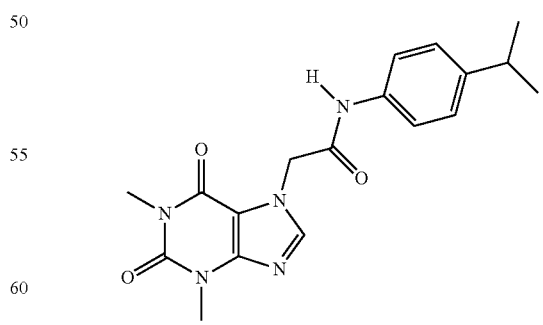

or a pharmaceutically acceptable salt thereof.

In certain embodiments, the TRPA1 antagonist used in the methods described herein is a compound represented by formula II or a pharmaceutically acceptable salt thereof:

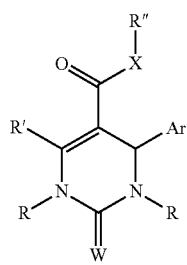

wherein, independently for each occurrence,
each W is O is S;
each R is hydrogen or lower alkyl;
R' is alkyl or aryl, each optionally substituted with one to five substituents selected from the group consisting of alkyl, alkenyl, alkynyl, halo, haloalkyl, haloalkenyl, fluoroalkyl, hydroxy, alkoxy, alkyenyloxy, alkynyloxy, carbocycyloxy, heterocycyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the alkyl or aryl group through an alkylene moiety;
X is O or NR";
R" is alkyl, alkenyl, alkynyl, aryl, heteroaryl, heterocycyl, carbocycyl, aralkyl, heteroaralkyl, heterocycylalkyl or carbocycylalkyl, each optionally substituted with one to five substituents selected from the group consisting of alkyl, alkenyl, alkynyl, halo, haloalkyl, haloalkenyl, fluoroalkyl, hydroxy, alkoxy, alkyenyloxy, alkynyloxy, carbocycyloxy, heterocycyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substiuents bound to the alkyl, alkenyl, alkynyl, aryl, heteroaryl, heterocycyl, carbocycyl, aralkyl, heteroaralkyl, heterocycylalkyl or carbocycylalkyl group through an alkylene moiety; and
Ar is aryl, optionally substituted with one to five substituents selected from the group consisting of alkyl, alkenyl, alkynyl, halo, haloalkyl, haloalkenyl, fluoroalkyl, hydroxy, alkoxy, alkyenyloxy, alkynyloxy, carbocycyloxy, heterocycyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the aryl group through an alkylene moiety.

Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like.

Certain compounds of the invention and their salts may exist in more than one crystal form and the present invention includes each crystal form and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

The present invention also includes prodrugs. As used herein the term "prodrug" refers to an agent which is converted into the parent drug in vivo by some physiological chemical process (e.g., a prodrug on being brought to the physiological pH is converted to the desired drug form). Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a prodrug would be a compound of the present invention wherein it is administered as an ester (the "prodrug") to facilitate transmittal across a cell membrane where water solubility is not beneficial, but then it is metabolically hydrolyzed to the carboxylic acid once inside the cell where water solubility is beneficial. Prodrugs have many useful properties. For example, a prodrug may be more water soluble than the ultimate drug, thereby facilitating intravenous administration of the drug. A prodrug may also have a higher level of oral bioavailability than the ultimate drug. After administration, the prodrug is enzymatically or chemically cleaved to deliver the ultimate drug in the blood or tissue.

Exemplary prodrugs upon cleavage release the corresponding free acid, and such hydrolyzable ester-forming residues of the compounds of this invention include but are not limited to carboxylic acid substituents (e.g., —$C(O)_2H$ or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$) alkyl.

Other exemplary prodrugs release an alcohol or amine of a compound of the invention wherein the free hydrogen of a hydroxyl or amine substituent is replaced by ($C_1$-$C_6$)alkanoyloxymethyl, 1-(($C_1$-$C_6$)alkanoyloxy)ethyl, 1-methyl-1-(($C_1$-

$C_6$)alkanoyloxy)ethyl, ($C_1$-$C_6$)alkoxycarbonyl-oxymethyl, N—($C_1$-$C_6$)alkoxycarbonylamino-methyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O($C_1$-$C_6$)alkyl)$_2$ or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1991), and *Protective Groups in Organic Synthesis* (T. Green and P. Wuts; 3rd Edition; John Wiley and Sons, 1999).

For example, a hydroxy group may be protected as an ether (—OR) or an ester (—OC(═O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(═O)CH$_3$, —OAc).

For example, an aldehyde or ketone group may be protected as an acetal or ketal, respectively, in which the carbonyl group (C(═O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(═O)R) or a urethane (—NRC(═O)OR), for example, as: a methyl amide (—NHC(═O)CH$_3$); a benzyloxy amide (—NHC(═O)OCH$_2$C$_6$H$_5$NHCbz); as a t-butoxy amide (—NHC(═O)OC(CH$_3$)$_3$, —NHBoc); a 2-biphenyl-2-propoxy amide (—NHC(═O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—SCH$_2$NHC(═O)CH$_3$).

3. INDICATIONS

Movement of ions across cellular membranes is carried out by specialized proteins. TRP channels are one large family of non-selective cation channels that function to help regulate ion flux and membrane potential. Non-selective cation channels such as TRPA1 modulate the flux of calcium and sodium ions across cellular membranes. Sodium and calcium influx leads to depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPA1 also alters the intracellular free calcium concentration. Calcium is a ubiquitous second messenger molecule within the cell, so alterations in intracellular calcium levels have profound effects on signal transduction and gene expression. As a result, activation of non-selective cation channels such as TRPA1 can lead to changes in gene expression and cellular phenotype. Gene expression events include, but are not limited to, production of mRNAs encoding cell surface receptors, ion channels, and kinases. These changes in gene expression can lead to hyperexcitability in that cell.

Modulating the function of TRPA1 proteins provides a means of modulating calcium homeostasis, sodium homeostasis, membrane polarization, and/or intracellular calcium levels, and compounds that can modulate TRPA1 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

4. BIOLOGICAL-WARFARE AGENTS

A subject may be exposed to a biological-warfare agent, e.g., by inhalation or by contact with the skin. If a TRPA1 antagonist is administered, the symptoms or injuries resulting from the exposure to the biological-warfare agents can be reduced, prevented, or both. The TRPA1 antagonist can be administered to a subject before, during, or following such exposure and is therefore administered within 24 hours, 18 hours, 6 hours, 4 hours, 3 hours, 2 hours, 1 hour, 30 minutes, 20 minutes, 10 minutes, 5 minutes, one minute, or thirty seconds before or after such exposure. The TRPA1 antagonist can be administered prophylactically, when exposure to an agent is anticipated. It can also be administered after exposure to the biological-warfare agent.

Injuries resulting from the exposure to biological-warfare agents are known in the art and include any physical injuries, such as injuries to the skin, eyes, respiratory tract, musculoskeletal system, circulatory system, gastrointestinal tract, central nervous system, peripheral nervous system, heart, liver, lungs, and kidneys. Exemplary symptoms or injuries resulting from the exposure to biological-warfare agents include inflammation, burn, itch, pain, rash, blisters, sweating, muscle twitching, nausea, vomiting, diarrhea, weakness, loss of consciousness, convulsions, muscular twitching, paralysis, secretions (from the mouth, nose, or lung for example), difficulty breathing, blurred vision, eye pain, lacrimation, red eyes, shortness of breath, coughing, phlegm production and narrowing of the airways, headaches, tremors, dizziness, numbness or tingling, anxiety, insomnia, depression, emotional instability, and even death. The term "biological-warfare agent" includes all of those agents classified as schedule 1, 2, and 3 agents under the Biological Weapons Convention of 1972 and may be in liquid form, gas form, solid form, or combinations thereof. Exemplary agents are described in further detail below and include, for example, *Bacillus anthracis* (anthrax), *Burkholderia mallei* (glanders), *Burkholderia pseudomallei* (melioidosis), *Clostridium botulinum* toxin (botulism), Ebola virus, *Francisella tularensis* (tularemia), Marburg virus, *Vibrio cholerae* (cholera), alphaviruses, Venezuelan equine encephalitis virus, eastern equine encephalitis virus, western equine encephalitis virus, filoviruses, arenaviruses, Lassa virus, Machupo virus or *Yersinia pestis* (plague).

Plague

Plague is a severe and potentially deadly bacterial infection. Plague is caused by the organism *Yersinia pestis*. The three most common forms of plague are: Bubonic plague—an infection of the lymph nodes; Pneumonic plague—an infection of the lungs; and Septicemic plague—an infection of the blood. The time between being infected and developing symptoms is typically 2 to 10 days, but may be as short as a few hours for pneumonic plague. Antibiotics are often used to treat plague. For example, antibiotics such as streptomycin, chloramphenicol, tetracyclines, sulfonamides (e.g., trimethoprim-sulfamethoxazole), gentamicin, doxycycline, and fluoroquinolones (e.g., ciprofloxacin) have been used to treat plague.

Streptomycin is effective against *Y. pestis*, and the drug of choice for treatment of plague, particularly the pneumonic form. Therapeutic effect may be expected with 30 mg/kg/day (up to a total of 2 g/day) in divided doses given intramuscularly, to be continued for a full course of 10 days of therapy or until 3 days after the patient's temperature has returned to normal. Gentamicin has been found to be effective in animal studies, and is used to treat human plague patients.

Chloramphenicol is a suitable alternative to aminoglycosides in the treatment of bubonic or septicaemic plague, and is the drug of choice for treatment of patients with *Y. pestis* invasion of tissue spaces into which other drugs pass poorly or not at all (such as plague meningitis, pleuritis, or endophthalmitis). Dosage should be 50 mg/kg/day administered in divided doses either parenterally or, if tolerated, orally for 10 days. Chloramphenicol may be used adjunctively with aminoglycosides.

Tetracyclines are bacteriostatic but effective in the primary treatment of patients with uncomplicated plague. An oral loading dose of 15 mg/kg tetracycline (not to exceed 1 g total) should be followed by 25-50 mg/kg/day (up to a total of 2 g/day) for 10 days. Tetracyclines may also be used adjunctively with other antibiotics.

Sulfonamides have been used extensively in plague treatment and prevention; however, some studies have shown higher mortality, increased complications, and longer duration of fever as compared with the use of streptomycin, chloramphenicol or tetracycline antibiotics. Sulfadiazine is typically given as a loading dose of 2-4 g, followed by a dose of 1 g every 4-6 hours for a period of 10 days. In children, the oral loading dose is 75 mg/kg, followed by 150 mg/kg/day orally in six divided doses. The combination drug trimethoprim-sulfamethoxazole has been used both in treatment and prevention of plague.

Fluoroquinolones, such as ciprofloxacin, have been shown to have good effect against *Y. pestis* in both in vitro and animal studies. Ciprofloxacin is bacteriocidal and has broad spectrum activity against most Gram-negative aerobic bacteria, including Enterobacteriaceae and *Pseudomonas aeruginosa*, as well as against many Gram-positive bacteria.

Anthrax

Anthrax is an acute disease caused by the bacteria *Bacillus anthracis*. Most forms of the disease are lethal, and it affects humans and other animals. There are effective vaccines against anthrax, and some forms of the disease respond well to antibiotic treatment. Early antibiotic treatment of anthrax is essential—delay significantly lessens chances for survival. Treatment for anthrax infection includes large doses of intravenous and oral antibiotics, such as, for example, fluoroquinolones, like ciprofloxacin (cipro), tetracyclines, like doxycycline, erythromycin, vancomycin and penicillin.

5. PHARMACEUTICAL COMPOSITIONS

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

The tablets, and other solid dosage forms of the pharmaceutical compositions disclosed herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The formulations disclosed herein can be delivered via a device. Exemplary devices include, but are not limited to, a catheter, wire, stent, or other intraluminal device. Further exemplary delivery devices also include a patch, bandage, mouthguard, or dental apparatus. Transdermal patches have the added advantage of providing controlled delivery of a compound disclosed herein to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Another example of a device is a metered dose aerosol dispenser containing an aerosol pharmaceutical composition for pulmonary or nasal delivery comprising an agent that inhibits a TRPA1-mediated current with an $IC_{50}$ of 1 micromolar or less. For instance, it can be a metered dose inhaler, a dry powder inhaler or an air-jet nebulizer.

Ophthalmic formulations, eye ointments, drops, solutions and the like, are also contemplated as being within the scope of this invention.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intraorbitally, intracardially, intradermally, intraperitoneally, transtracheally, subcutaneously, subcuticularly, intraarticularly, subcapsularly, subarachnoidly, intraspinally, intrasternally or by inhalation.

Particularly useful modes of administration include topical administration, intramuscular injection, inhalation, topical ocular administration (e.g., via eye drops), or oral administration.

6. COMBINATION THERAPY

Another aspect of the invention provides a conjoint therapy wherein one or more other therapeutic agents are administered with the TRPA1 modulators. For example, the additional therapeutic agent can be a therapeutic agent that is art-recognized as being useful to treat the disease or condition being treated by the compound of the present invention.

The combination therapy contemplated by the invention includes, for example, administration of a TRPA1 antagonist, or a pharmaceutically acceptable salt thereof, and additional agent(s) in a single pharmaceutical formulation as well as administration of a compound of the invention, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time. In other words, such conjoint treatment may be achieved by way of the simultaneous, sequential, or separate dosing of the individual components of the treatment.

It should further be understood that the combinations included within the invention are those combinations useful for their intended purpose. The therapeutic agents set forth below are illustrative for purposes and not intended to be limited. The combinations, which are part of this invention, can be the compounds of the present invention and at least one additional therapeutic agent selected from the lists below. The combination can also include more than one additional agent, e.g., two or three additional agents if the combination is such that the formed composition can perform its intended function.

In certain embodiments, two or more compounds of the invention are conjointly administered. When two or more compounds of the invention are conjointly administered, the two or more compounds may have a similar selectivity profile and functional activity, or the two or more compounds may have a different selectivity profile and functional activity. By way of example, the two or more compounds may both be approximately 10-, 100-, or 1000-fold selective for antagonizing a function of TRPA1 over TRPV1, TRPV5, and TRPV6 (e.g., the two or more compounds have a similar selectivity profile), and further may inhibit a function of TRPA1 with a similar $IC_{50}$ (e.g., a similar functional activity). Alternatively, the one of the two or more compounds may selectively inhibit TRPA1 while the other of the two or more compounds inhibits both TRPA1 and TRPV1 (e.g., the two or more compounds have differing selectivity profiles). Administration of combinations of two or more compounds of the invention having similar or differing properties is contemplated by the invention.

In certain embodiments, a compound of the invention is conjointly administered with one or more additional compounds that antagonize the function of a different channel. By way of example, a compound of the invention may be conjointly administered with one or more compounds that antagonize TRPV1, TRPM8, and/or TRPV3. The compound(s) that antagonize TRPV1, TRPM8, or TRPV3 may be selective for TRPV1, TRPM8 or TRPV3 (e.g., inhibit TRPV1 or TRPV3 10, 100, or 1000 fold more strongly than TRPA1). Alternatively, the compound(s) that antagonize TRPV1 or TRPV3 may cross react with other TRP channels.

In certain embodiments, a TRPA1 antagonist is conjointly administered with one or more additional agents or therapeutic regimens appropriate for the particular injury being treated. For example, current treatments for injuries caused by exposure to biological-warfare agents include treatment with antibiotics and/or antivirals. Any of these agents can be combined with the TRPA1 antagonists described herein.

In certain embodiments, an antibiotic to be used in combination with a TRPA1 antagonists is selected from the group consisting of, Amikacin, Gentamicin, Kanamycin, Neomycin, Netilmicin, Streptomycin, Tobramycin, Paromomycin, Geldanamycin, Herbimycin, Loracarbef, Ertapenem, Doripenem, Imipenem/Cilastatin, Meropenem, Cefadroxil, Cefazolin, Cefalotin, Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Telavancin, Azithromycin, Clarithromycin, Dirithromycin, Erythromycin, Roxithromycin, Troleandomycin, Telithromycin, Spectinomycin, Aztreonam, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Temocillin, Ticarcillin, Bacitracin, Colistin, Polymyxin B, Ciprofloxacin, Enoxacin, Gatifloxacin, Levofloxacin, Lomefloxacin, Moxifloxacin, Norfloxacin, Ofloxacin, Trovafloxacin, Grepafloxacin, Sparfloxacin, Temafloxacin, Mafenide, Sulfonamidochrysoidine, Sulfacetamide, Sulfadiazine, Silver sulfadiazine, Sulfamethizole, Sulfanilimide, Sulfasalazine, Sulfisoxazole, Trimethoprim, Trimethoprim-Sulfamethoxazole (Co-trimoxazole) (TMP-SMX), Demeclocycline, Doxycycline, Minocycline, Oxytetracycline, Tetracycline, Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin, Thiamphenicol, Timidazole, Dapsone and Clofazimine.

In certain embodiments, an antiviral to be used in combination with a TRPA1 antagonist is selected from the group consisting of anti-viral agents selected from the group consisting of immunoglobulins, amantadine, interferons, nucleotide analogues, and protease inhibitors. Specific examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

7. DOSAGES

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. For example, the dose can be 1-50, 1-25, or 5-10 mg/kg.

8. DISEASE AND INJURY MODELS

Compounds that antagonize TRPA1 function may be useful in the prophylaxis and treatment of any of the foregoing injuries, diseases, disorders, or conditions. In addition to in vitro assays of the activity of these compounds, their efficacy can be readily tested in one or more animal models. Compounds that may reduce pain or other undesirable symptoms in the animals can be readily tested by observing behavioral and/or physical characteristics of challenged animals in the presence versus the absence of the test compound(s) or procedure.

Part I: Testing TRPA1 Antagonists in Aerosol Challenge Models of Infection

Animals will be aerosol challenged with a dose of 10 to 100 $LD_{50}s$ of either *B. anthracis* spores (Ames) $LD_{50}$, $3.4\times10^4$ CFU/mL, *Y. pestis* (CO92) $LD_{50}$, $2.3\times10^4$ CFU/mL, *F. tularensis* (Schu4) $LD_{50}$ 100 CFU/mL, *B. mallei* (China 7) $LD_{50}$ $3\times10^4$ CFU/mL or *B. pseudomallei* (1026b) $3\times10^4$ CFU/mL. Treatment will begin 24 hours after challenge (post-exposure prophylaxis (PEP)). Each initial therapeutic study will be organized as follows (when possible looking at multiple therapeutics with the same administration route to shared control groups).

For *B. anthracis* spores, it is known that due to the persistence of ungerminated spores in the lungs of the challenged animals, a minimum treatment duration of 14 days is required. *F. tularensis*, *B. mallei* and *B. pseudomallei* also require 14 days of treatment. For *Y. pestis*, a 5-day treatment is required. Dose and administration schedule will vary based on the TRPA1 antagonist used. Combinations of TRPA1 antagonists and, for example, antibiotics such as doxycycline, will also be used.

Part II: Evaluation of Rescue if Treatment is Initiated at Later Time Points

Mice (e.g., 10/group) will be challenged by aerosol with 10 to 100 $LD_{50}s$ of the respective bacterial agent. Treatment will be initiated at 24, and 42 hours after challenge for anthrax and plague experiments. Dose, route of administration and duration of treatment will be based on previous data from Part I.

EXEMPLIFICATION

The invention now being generally described, it will be more readily understood by reference to the following, which is included merely for purposes of illustration of certain aspects and embodiments of the present invention, and is not intended to limit the invention.

Example 1

General Synthetic Methods

A general synthetic scheme is shown in FIG. 1.
Step 1: Preparation of Compound 2

To ketone 1 in isopropyl acetate is added HBr (47%). Bromine is added to this mixture at 18-24° C. The mixture is stirred for 4 hours and monitored by LCMS. The reaction mixture is added to a mixture of water and dichloromethane at 5-10° C. The mixture is stirred and warmed to 18-24° C. The phases are separated and the organic phase is washed with saturated sodium bicarbonate solution once, then twice with water. The solution is concentrated under vacuum to yield Compound 2.

Step 2: Preparation of Aminothiazole 3

Bromide 2 is dissolved in dichloromethane and added to a suspension of thiourea in ethanol at 0-5° C. and monitored by LCMS. Isopropyl acetate is added over 30 min at 0-5° C. The formed mixture is stirred for 2 hrs at 0-5° C. The product is filtered and washed with isopropyl acetate. After drying under vacuum at 50° C., the product 3 is isolated.

Step 3: Coupling to 4

Acid 4 and 4-dimethylaminopyridine are suspended in DMF. A solution of 1,1'-carbonyldiimidazole in DMF is added at 18-24° C. After stirring for 30 minutes, the solution is heated to 50° C. At this temperature a solution of amine 3 in DMF is added. The line is rinsed with DMF. The mixture is heated for 6.5 hrs at 50° C. and subsequently at room temperature for two days. The product suspension is heated to 50° C. and 180 mL of water is added. The suspension is cooled to 18-24° C. over about 2 hours and filtered. The product is washed with water in two portions. Wet product is isolated. The wet crude product is suspended in ethanol and heated to reflux for 30 min. The suspension is cooled to room temperature. The product was filtered and washed with ethanol. After drying, Compound 5 is isolated.

Additional compounds can be synthesized as described in WO 2009/002933, which is hereby incorporated by reference in its entirety.

Example 2

High Throughput Screening Assay

The assay depended on detection of the rise in intracellular $Ca^{2+}$ concentration ($[Ca^{2+}]_i$) following channel activation in cells inducibly expressing the TRPA1 channel. $Ca^{2+}$ rise was quantified with the use of fluorescent $Ca^{2+}$ indicators that were loaded into cells and thereafter indicated the $[Ca^{2+}]_i$.

$Ca^{2+}$ influx followed activation of the TRPA1 channel. Compounds inhibiting the $[Ca^{2+}]_i$ rise were considered hits for further investigation.

The commercially available HEK293/TREx line (Invitrogen) was stably transfected with a TRPA1 construct (specifically a construct encoding a TRPA1 protein with an amino acid sequence depicted in SEQ ID NO: 1 of WO 2007/073505, which is hereby incorporated by reference in its entirety) and screened by conventional calcium imaging to find clones with TRPA1 expression following stimulation with 1 μg/mL tetracycline. These cells were maintained in the growth medium recommended by the manufacturer supplemented with 100 μg/mL hygromycin to promote retention of the TRPA1 construct. After growing to near confluency, cells were plated at a density of about 25,000 cells/well in 384-well CellBind plates (Corning) in the presence of 1 μg/mL tetracycline, and allowed to grow for 20-30 hrs. A nearly confluent monolayer resulted. Cells were then loaded with $Ca^{2+}$ dye: Fura-2/AM or Fluo4/AM was added to the wells to a final concentration of 2 or 1 respectively, and incubated for ~60 min at room temperature. Supernatant was then removed from the cells by inverting plates with a sharp flick, and Hank's Balanced Salt Solution (HBSS; 0.185 g/L D-glucose, 0.9767 g/L $MgSO_4$ (anhydrous), 0.4 g/L KCl, 0.06 g/L $KH_2PO_4$ (anhydrous), 0.35 g/L $NaHCO_3$, 8.0 g/L NaCl, and 0.04788 g/L $Na_2HPO_4$ (anhydrous); pH 7.4) was then added to each well. Following recovery from loading, cells were assayed using the Hamamatsu FDSS 6000 system, which permitted illumination alternately at 340 nM and 380 nM for Fura-2 experiments, or at 485 nM for Fluo4 experiments. Frames were acquired at a rate of 0.2 Hz. For the screening assay, a diluted stock (at 50 μM) of compounds to be tested was added to each well for 2 minutes following the collection of a short (4 frame) baseline. AITC (allylisothiocyanate) was then added to each well, achieving a final concentration of 10 μM each compound and 7.5 μM AITC. Data were collected for at least 3 minutes following addition of AITC, and evaluated for the $[Ca^{2+}]_i$, which is proportional to the fluorescent intensity (for Fluo4) or the F340/F380 ratio (for Fura-2). Negative controls consisted of HEK293/TREx TRPA1 cells exposed to AITC, but no compound. Positive control cells were usually HEK293/TREx ("parental") cells exposed to AITC but no compound, but sometimes normal HEK/293 TREx TRPA1 cells were also used, but not exposed to AITC or compound. These controls defined a screening window, and "hits" were defined as those compounds inhibiting the fluorescence response by at least 40%. $IC_{50}$ values were determined for compounds defined as "hits." The Fluo4 cell-based fluorescence assay was used to determine the intracellular $Ca^{2+}$ concentration in the presence of varying drug concentration. To determine $IC_{50}$ values, concentrations tested were 40 μM, 20 μM, 10 μM, 5 μM, 2.5 μM, 1.25 μM, and 0.625 μM. Compounds were tested in triplicate at all concentrations. Standard software was used to fit $IC_{50}$ curves.

Additionally or alternatively, potency can be represented as % inhibition of a response in the presence (of a given concentration of compound) versus the absence of compound or in comparison to a control compound. For example, efficacy can be represented as % inhibition of ion flux in the presence versus the absence of compound.

Example 3

Patch Clamp Experiments

Patch clamp experiments permit the detection of currents through the TRPA1 channel in the cell line described above. The whole-cell configuration of the patch clamp technique was used to test the compounds described herein. In normal whole-cell patch clamp recordings, a glass electrode is brought into contact with a single cell and a high-resistance (gigaohm) seal is established with the cell membrane. The membrane is then ruptured to achieve the whole-cell configuration, permitting control of the voltage of the cell membrane and measurement of currents flowing across the membrane using the amplifier attached to the electrode and resulting in the replacement of cytoplasm with the pipette solution.

HEK293/TREx TRPA1 cells were induced in the presence of 1 μg/mL tetracycline for 20-48 hours, removed from growth plates, and replated at low density (to attain good single-cell physical separation) on glass coverslips for measurement. In some cases, cells were grown in low density overnight on glass coverslips. Potential blockers were tested for ability to block current in the continued presence of AITC.

Example 4

Biological Studies

Four groups of mice (ten mice per group) were exposed to about $90 \times LD_{50}$ for Plague (*Yersinia pestis*): (Group 1) untreated; (Group 2) low-dose doxycycline, which was administered 42 hours after exposure to mimic real-world conditions; (Group 3) HC-030031 (40) administered one day prior to exposure, and then low dose doxycycline 42 hours post exposure; and (Group 4) high dose Cipro administered 24 hrs post exposure. Results are shown in FIG. 3. The key readout is mortality.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

The invention claimed is:

1. A method of preventing or treating an injury resulting from exposure to a biological warfare agent comprising administering to a subject in need thereof an effective amount of a TRPA1 antagonist or a pharmaceutically acceptable salt thereof, wherein the biological warfare agent is selected from the group consisting of *Bacillus anthracis* (anthrax), *Burkholderia mallei* (glanders), *Burkholderia psuedomallei* (melioidosis), *Clostridium botulinum* toxin (botulism), Ebola virus, *Francisella tularensis* (tularemia), Marburg virus, *Vibrio cholera* (cholera), alphaviruses, Venezuelan equine encephalitis virus, eastern equine encephalitis virus, western equine encephalitis virus, filoviruses, arenaviruses, Lassa virus, Machupo virus and *Yersinia pestis* (plague).

2. The method of claim 1, wherein the TRPA1 antagonist is selected from the group consisting of compounds of formula I $$X-(\underset{R}{\overset{R}{C}})_m-L-(\underset{R}{\overset{R}{C}})_n-R^3 \quad \text{I}$$

wherein,

R is hydrogen, $C_1$-$C_6$ alkyl, $C_2$-$C_6$ alkenyl, $C_2$-$C_6$ alkynyl, halo, hydroxyl, alkoxy, amino, alkylamino, thiol, alkylthiol, nitro, or cyano, each of which is optionally substituted with one or two $R^{11}$;

X is

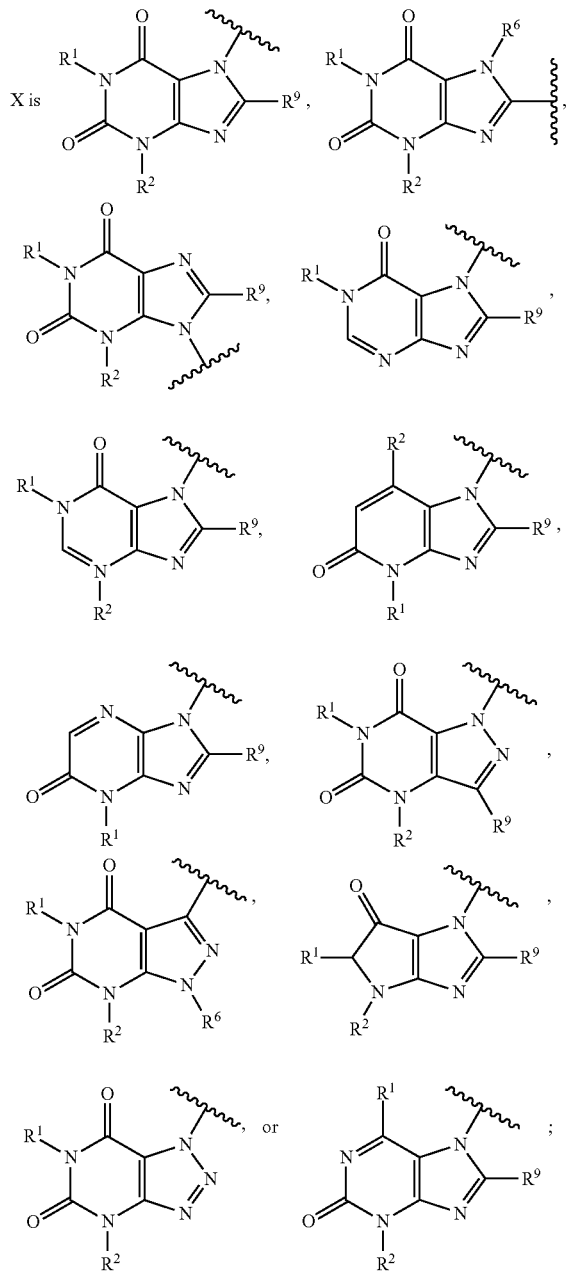

$R^1$ and $R^2$ are each independently hydrogen, $C_1$-$C_6$ alkyl, $C_2$-$C_6$ alkenyl, or $C_2$-$C_6$ alkynyl, each of which is optionally substituted with one to four $R^5$;

L is $NR^6SO_2$, $SO_2NR^6$, $C(O)NR^6$, $NR^6C(O)$, $C(S)NR^6$, $NR^6C(S)$, $OC(O)NR^6$, $NR^6C(O)O$, $NR6C(O)NR^6$, S, S(o), $S(O)_2$, $NR^6$, $CH_2$, O, $C(O)$, $C(O)NR^6SO_2$, $SO_2NR^6C(O)$, heteroarylene, or carbocyclylene;

$R^3$ is carbocyclyl, heterocyclyl, aryl, heteroaryl, or $R^{3a}$, each of which is optionally substituted with one to four $R^7$;

$R^{3a}$ is carbocyclylene, heterocyclylene, arylene, heteroarylene, each of which is substituted with one $R^{3b}$;

$R^{3b}$ is carbocyclyl, heterocyclyl, aryl, or heteroaryl, each of which is optionally substituted with one to four $R^7$;

each $R^5$ is independently halo, hydroxyl, alkoxy, amino, alkylamino, dialkylamino, cyano, nitro, amido, alkylamido, dialkylamido, thioyl, sulfonyl, carbocyclyl, heterocyclyl, aryl, or heteroaryl;

each $R^6$ is independently hydrogen, $C_1$-$C_6$ alkyl, $C_2$-$C_6$ alkenyl, hydroxy-$C_1$-$C_6$ alkyl, alkoxy-$C_1$-$C_6$ alkyl, cyanoalkyl, haloalkyl, arylalkyl, —S(O)alkyl, acyl, amino, amidyl, —S(O)H, —S(O)$_2$H, —S(O)$_2$OH, aryl, or alkoxyaryl;

each $R^7$ is independently $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, carbocyclyl, heterocyclyl, aryl, heteroaryl, carbocyclylalkyl, heterocyclylalkyl, arylalkyl, heteroarylalkyl, halo, hydroxyl, alkoxy, aryloxy, arylalkoxy, amino, alkylamino, dialkylamino, thioyl, alkylthioyl, sulfonyl, sulfonamidyl wherein the nitrogen of the sulfonamide is substituted with an alkyl, or wherein the nitrogen of the sulfonamide together with two carbons to which it is attached, forms a heterocyclyl, amido wherein the nitrogen of the amide is substituted with an alkyl, or wherein the nitrogen of the amide together with two carbons to which it is attached, forms a heterocyclyl urea, sulfonylurea, acyl, —C(O)aryl, —NHC(O)aryl, —C(O)NHaryl, —C(O)OH, —C(O)Oalkyl, nitro, or cyano, each of which is optionally substituted with one to three $R^8$;

each $R^8$ is independently $C_1$-$C_6$ alkyl, $C_2$-$C_6$ alkenyl, $C_2$-$C_6$ alkynyl, halo, $C_1$-$C_6$ haloalkyl, hydroxyl, alkoxy, aryloxy, amino, alkylamino, dialkylamino, thioyl, sulfonyl, sulfonamidyl, amido, —C(O)OH, —C(O)Oalkyl, urea, sulfonylurea, acyl, nitro, cyano, carbocyclyl, heterocyclyl, aryl, or heteroaryl, each of which is optionally substituted with one to three $C_1$-$C_6$ alkyl, $C_1$-$C_6$ haloalkyl, or halo;

$R^9$ is independently hydrogen, $C_1$-$C_6$ alkyl, $C_2$-$C_6$ alkenyl, $C_2$-$C_6$ alkynyl, halo, $C_1$-$C_6$ haloalkyl, hydroxyl, alkoxy, aryloxy, arylalkoxy, amino, alkylamino, dialkylamino, thioyl, alkylthioyl, sulfonyl, sulfonamidyl, amido, urea, sulfonylurea, acyl, nitro, or cyano, each of which is optionally substituted with one to three $R^8$;

each $R^{11}$ is independently $C_1$-$C_6$ alkyl, $C_2$-$C_6$ alkenyl, $C_2$-$C_6$ alkynyl, halo, hydroxyl, alkoxy, oxo, aryloxy, amino, alkylamino, dialkylamino, C(O)OH, —C(O)Oalkyl, thioyl, sulfonyl, sulfonamidyl, amido, urea, sulfonylurea, acyl, nitro, cyano, cyclyl, heterocyclyl, aryl, or heteroaryl; and each of m and n is independently 0, 1, 2, 3, 4, 5 or 6;

compounds of formula II

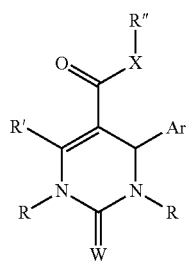

wherein, independently for each occurrence,
each W is O or S;
each R is hydrogen or lower alkyl;
R' is alkyl or aryl, each optionally substituted with one to five substituents selected from the group consisting of alkyl, alkenyl, alkynyl, halo, haloalkyl, haloalkenyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, alkoxysulfonyl, haloalkoxysulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfinyl, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the alkyl or aryl group through an alkylene moiety;
X is O or NR'';
R'' is alkyl, alkenyl, alkynyl, aryl, heteroaryl, heterocyclyl, carbocyclyl, aralkyl, heteroaralkyl, heterocyclylalkyl, or carbocyclylalkyl, each optionally substituted with one to five substituents consisting of alkyl, alkenyl, alkynyl, halo, haloalkyl, haloalkenyl, fluoroalkyl, hydroxy, alkoxy, alkenyloxy, alkynyloxy, carbocycloxy, heterocycloxy, haloalkoxy, fluoroalkyloxy, sulfhydryl, alkylthio, haloalkylthio, fluoroalkylthio, alkenylthio, alkynylthio, sulfonic acid, alkylsulfonyl, alkoxysulfonyl, haloalkoxysulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfinyl, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinylkoxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the alkyl, alkenyl, alkynyl, aryl, heteroaryl, heterocyclyl, carbocyclyl, aralkyl, heteroaralkyl, heterocyclylalkyl, or carbocyclylalkyl group through an alkylene moiety; and
Ar is aryl, optionally substituted with one to five substituents selected from the group consisting of alkyl, alkenyl, alkynyl, aryl, heteroaryl, heterocycl, carbocycl, aralkyl, heteroaralkyl, heterocycylalkyl, or carbocyclalkyl, each optionally substituted with one to five substituents selected from the group consisting of alkyl, alkenyl, alkynyl, halo, haloalkyl, haloalkenyl, fluoroalkyl, hydroxy, alkoxy, alkenyloxy, alkynyloxy, carbocycyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, alkoxysulfonyl, haloalkoxysulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinul, haloalkoxysulfinyl, fluoroalkoxysulfinyl, alkenyloxyaulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinylkoxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the alkyl or aryl group through an alkylene moiety;
and pharmaceutically acceptable salts thereof.

3. The method of claim 1, wherein the TRPA1 antagonist is selected from the group consisting of

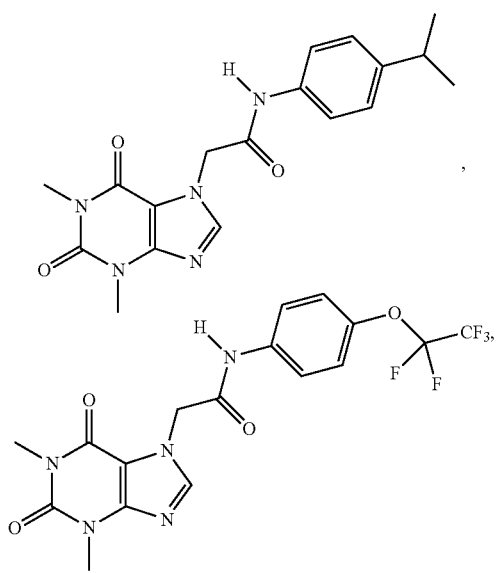, and pharmaceutically acceptable salts thereof.

4. The method of claim 2, wherein the TRPA1 antagonist is administered orally.
5. The method of claim 2, wherein the TRPA1 antagonist is administered via intramuscular injection.
6. The method of claim 2, wherein the TRPA1 antagonist is administered topically.
7. The method of claim 2, wherein the TRPA1 antagonist is administered by topical ocular administration.
8. The method of claim 2, wherein the TRPA1 antagonist is administered prior to the exposure to the biological-warfare agent.
9. The method of claim 2, wherein the TRPA1 antagonist is administered after exposure to the biological-warfare agent.
10. The method of claim 2, wherein the biological-warfare agent is *Bacillus anthracis* (anthrax).
11. The method of claim 2, wherein the biological-warfare agent is *Yersinia pestis* (plague).
12. The method of claim 2, wherein the subject is human.
13. The method of claim 2, further comprising co-administering an antibiotic to the subject in need thereof.
14. The method of claim 13, wherein the ant

SEQUENCE LISTING

```
<160> NUMBER OF SEQ ID NOS: 1

<210> SEQ ID NO 1
<211> LENGTH: 1119
<212> TYPE: PRT
<213> ORGANISM: Homo sapiens
```

```
<400> SEQUENCE: 1

Met Lys Arg Ser Leu Arg Lys Met Trp Arg Pro Gly Glu Lys Glu
1               5                   10                  15

Pro Gln Gly Val Val Tyr Glu Asp Val Pro Asp Asp Thr Glu Asp Phe
            20                  25                  30

Lys Glu Ser Leu Lys Val Val Phe Glu Gly Ser Ala Tyr Gly Leu Gln
        35                  40                  45

Asn Phe Asn Lys Gln Lys Lys Leu Lys Arg Cys Asp Asp Met Asp Thr
    50                  55                  60

Phe Phe Leu His Tyr Ala Ala Glu Gly Gln Ile Glu Leu Met Glu
65                  70                  75                  80

Lys Ile Thr Arg Asp Ser Ser Leu Glu Val Leu His Glu Met Asp Asp
                85                  90                  95

Tyr Gly Asn Thr Pro Leu His Cys Ala Val Glu Lys Asn Gln Ile Glu
                    100                 105                 110

Ser Val Lys Phe Leu Leu Ser Arg Gly Ala Asn Pro Asn Leu Arg Asn
                115                 120                 125

Phe Asn Met Met Ala Pro Leu His Ile Ala Val Gln Gly Met Asn Asn
    130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
                165                 170                 175

Asn Ser Glu Ala Leu Gln Ile Leu Leu Asn Lys Gly Ala Lys Pro Cys
        180                 185                 190

Lys Ser Asn Lys Trp Gly Cys Phe Pro Ile His Gln Ala Ala Phe Ser
    195                 200                 205

Gly Ser Lys Glu Cys Met Glu Ile Ile Leu Arg Phe Gly Glu Glu His
210                 215                 220

Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
                245                 250                 255

Met Cys Leu Asp Asn Gly Ala Gln Ile Asp Pro Val Glu Lys Gly Arg
                260                 265                 270

Cys Thr Ala Ile His Phe Ala Ala Thr Gln Gly Ala Thr Glu Ile Val
            275                 280                 285

Lys Leu Met Ile Ser Ser Tyr Ser Gly Ser Val Asp Ile Val Asn Thr
        290                 295                 300

Thr Asp Gly Cys His Glu Thr Met Leu His Arg Ala Ser Leu Phe Asp
305                 310                 315                 320

His His Glu Leu Ala Asp Tyr Leu Ile Ser Val Gly Ala Asp Ile Asn
                325                 330                 335

Lys Ile Asp Ser Glu Gly Arg Ser Pro Leu Ile Leu Ala Thr Ala Ser
                    340                 345                 350

Ala Ser Trp Asn Ile Val Asn Leu Leu Leu Ser Lys Gly Ala Gln Val
            355                 360                 365

Asp Ile Lys Asp Asn Phe Gly Arg Asn Phe Leu His Leu Thr Val Gln
    370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
                405                 410                 415
```

-continued

```
Leu His Tyr Ala Cys Arg Gln Gly Gly Pro Gly Ser Val Asn Asn Leu
            420                 425                 430

Leu Gly Phe Asn Val Ser Ile His Ser Lys Ser Lys Asp Lys Lys Ser
            435                 440                 445

Pro Leu His Phe Ala Ala Ser Tyr Gly Arg Ile Asn Thr Cys Gln Arg
            450                 455                 460

Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                485                 490                 495

Val Val Gln Leu Leu Leu Lys Lys Gly Ala Leu Phe Leu Ser Asp His
            500                 505                 510

Asn Gly Trp Thr Ala Leu His His Ala Ser Met Gly Gly Tyr Thr Gln
            515                 520                 525

Thr Met Lys Val Ile Leu Asp Thr Asn Leu Lys Cys Thr Asp Arg Leu
            530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
            580                 585                 590

Lys Glu Val Val Leu Thr Ile Ile Arg Ser Lys Arg Trp Asp Glu Cys
            595                 600                 605

Leu Lys Ile Phe Ser His Asn Ser Pro Gly Asn Lys Cys Pro Ile Thr
            610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
            660                 665                 670

Thr Pro Thr Gln Asp Val Ile Tyr Glu Pro Leu Thr Ala Leu Asn Ala
            675                 680                 685

Met Val Gln Asn Asn Arg Ile Glu Leu Leu Asn His Pro Val Lys Lys
            690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
            755                 760                 765

Leu Ile Lys Thr Cys Met Ile Leu Val Phe Leu Ser Ser Ile Phe Gly
            770                 775                 780

Tyr Cys Lys Glu Ala Gly Gln Ile Thr Gln Gln Lys Arg Asn Tyr Thr
785                 790                 795                 800
```

-continued

```
Met Asp Ile Ser Asn Val Leu Glu Trp Ile Ile Tyr Thr Thr Gly Ile
            805                 810                 815
Ile Thr Val Leu Pro Leu Thr Val Glu Ile Pro Ala His Leu Gln Trp
            820                 825                 830
Gln Cys Gly Ala Ile Ala Val Tyr Thr Tyr Trp Met Asn Thr Leu Leu
            835                 840                 845
Tyr Leu Gln Arg Thr Glu Asn Cys Gly Ile Phe Ile Val Met Leu Glu
        850                 855                 860
Val Ile Leu Lys Thr Leu Leu Arg Ser Thr Val Val Phe Ile Phe Leu
865                 870                 875                 880
Leu Leu Ala Phe Gly Leu Ser Phe Tyr Ile Leu Leu Asn Leu Gln Asp
                885                 890                 895
Pro Thr Ser Ser Pro Leu Leu Ser Ile Ile Gln Thr Thr Ser Met Met
                900                 905                 910
Leu Gly Asp Ile Asn Tyr Arg Glu Ser Thr Leu Glu Pro Tyr Leu Arg
            915                 920                 925
Asp Glu Leu Ala His Pro Val Leu Ser Thr Ala Gln Leu Val Ser Thr
            930                 935                 940
Thr Ile Thr Val Pro Ile Val Leu Met Asn Leu Leu Ile Gly Leu Ala
945                 950                 955                 960
Val Cys Asp Ile Ala Glu Val Gln Lys His Ala Ser Leu Lys Arg Ile
                965                 970                 975
Ala Met Gln Val Glu Leu His Thr Ser Leu Glu Lys Lys Leu Pro Leu
                980                 985                 990
Trp Phe Leu Arg Lys Val Asp Gln Lys Ser Thr Ile Val Tyr Pro Asn
            995                 1000                1005
Lys Pro Arg Ser Gly Gly Met Leu Thr His Ile Phe Cys Thr Leu
    1010                1015                1020
Thr Cys Thr Gly Glu Ile Arg Gln Glu Ile Pro Asn Ala Asp Lys
    1025            1030                1035
Ser Leu Glu Met Glu Ile Leu Lys Gln Lys Tyr Arg Leu Lys Asp
    1040            1045            1050
Leu Thr Phe Leu Leu Glu Lys Gln His Glu Leu Ile Lys Leu Ile
    1055            1060            1065
Ile Gln Lys Met Glu Ile Ile Ser Glu Thr Glu Asp Asp Asp Ser
    1070            1075            1080
His Cys Ser Phe Gln Asp Arg Phe Lys Lys Glu Gln Met Glu Gln
    1085            1090            1095
Arg Asn Ser Arg Trp Asn Thr Val Leu Arg Ala Val Lys Ala Lys
    1100            1105            1110
Thr His His Leu Glu Pro
    1115
```